(12) United States Patent
Spear

(10) Patent No.: US 10,310,717 B2
(45) Date of Patent: Jun. 4, 2019

(54) REAL-TIME PROBLEM REPORTING AND ALERT SYSTEM

(71) Applicant: Steven J. Spear, Brookline, MA (US)

(72) Inventor: Steven J. Spear, Brookline, MA (US)

(*) Notice: Subject to any disclaimer, the term of this patent is extended or adjusted under 35 U.S.C. 154(b) by 182 days.

(21) Appl. No.: 14/720,522

(22) Filed: May 22, 2015

(65) Prior Publication Data

US 2015/0346963 A1 Dec. 3, 2015

Related U.S. Application Data

(60) Provisional application No. 62/002,145, filed on May 22, 2014.

(51) Int. Cl.
| | | |
|---|---|---|
| *G06F 3/048* | (2013.01) | |
| *G06F 3/0484* | (2013.01) | |
| *G06F 11/07* | (2006.01) | |
| *G06Q 10/06* | (2012.01) | |

(Continued)

(52) U.S. Cl.
CPC ...... *G06F 3/04842* (2013.01); *G06F 3/04847* (2013.01); *G06F 11/0709* (2013.01); *G06F 11/0751* (2013.01); *G06F 11/0772* (2013.01); *G06F 11/0784* (2013.01); *G06Q 10/06* (2013.01); *G06Q 10/10* (2013.01); *G06Q 50/22* (2013.01)

(58) Field of Classification Search
CPC ....................................................... G06F 3/048
See application file for complete search history.

(56) References Cited

U.S. PATENT DOCUMENTS

| | | | |
|---|---|---|---|
| 2005/0039192 A1* | 2/2005 | Chavez, Jr. ............... | G06F 1/28 719/318 |
| 2005/0055244 A1* | 3/2005 | Mullan ................... | G06Q 50/22 705/2 |

(Continued)

FOREIGN PATENT DOCUMENTS

| | | |
|---|---|---|
| JP | 3848864 B2 | 11/2006 |
| KR | 10-2007-0066419 A | 6/2007 |

OTHER PUBLICATIONS

International Search Report and Written Opinion for International Application No. PCT/US2015/032229 dated Sep. 9, 2015.

(Continued)

*Primary Examiner* — Pei Yong Weng
(74) *Attorney, Agent, or Firm* — Wolf, Greenfield & Sacks, P.C.

(57) ABSTRACT

Techniques for reporting problems within an organization include presenting choices to a worker through a menu-based interface. The choices may indicate conditions or problems and may be organized in levels such that selection of a first choice in one level determines choices presented in a subsequent level. The choices may include a type of problem and/or a severity of the problem. A report may contain information identified by the worker's selected choices, and a support person indicated as a recipient for the report may be identified based on the selections and a mapping that relates possible choices selected by a worker to support personnel. The support person may provide corrective instructions to the worker to resolve the problem. Aggregation of reports may identify of systemic problems within the organization.

29 Claims, 14 Drawing Sheets

(51) Int. Cl.
    *G06Q 10/10*    (2012.01)
    *G06Q 50/22*    (2018.01)

(56)            References Cited

U.S. PATENT DOCUMENTS

2006/0288095 A1* 12/2006 Torok .................... G06Q 10/08
                                                    709/223
2008/0249804 A1   10/2008 Kim
2011/0148915 A1*  6/2011 Kim ..................... G06F 1/1626
                                                    345/619
2013/0162426 A1   6/2013 Wiesner et al.

OTHER PUBLICATIONS

International Preliminary Report on Patentability for International Application No. PCT/US2015/032229 dated Dec. 1, 2016.

* cited by examiner

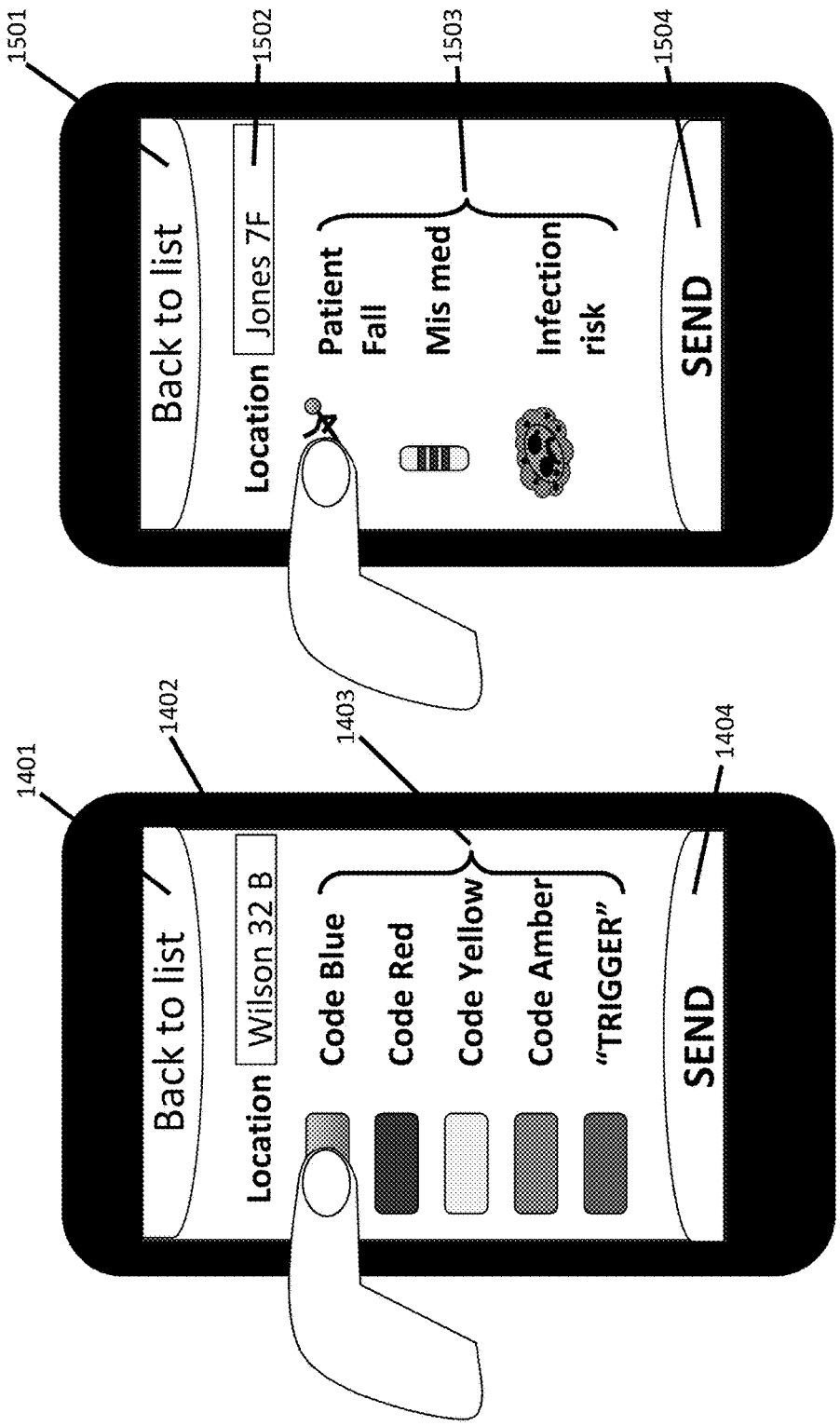

REAL-TIME PROBLEM REPORTING AND ALERT SYSTEM

RELATED APPLICATIONS

This Application claims priority under 35 U.S.C. § 119(e) to U.S. Provisional Application Ser. No. 62/002,145, entitled "REAL-TIME PROBLEM REPORTING AND ALERT SYSTEM" filed on May 22, 2014, which is herein incorporated by reference in its entirety.

FIELD OF THE APPLICATION

Described herein are systems and methods for electronically reporting conditions indicative of problems in an organization, and for analyzing information to identify problems and address them.

BACKGROUND

Throughout businesses and other organizations, problems arise that require corrective action. Such problems may come to the attention of management of the organization in any of a number of ways. For example, in a hospital, doctors, nurses or other healthcare workers may make reports of problems to the hospital's management organization.

The nature of the problem may impact the way that reports are delivered. Reports, for example, might be made verbally, such as over the phone, to a manager of a service center that can dispatch personnel to address the problem, if warranted. Alternatively, the reports might be made in a written form, which may be physically or electronically transmitted to the organization's management who may schedule service to address the problem.

SUMMARY

Systems and methods are provided herein for problem reporting. The system may be configured to facilitate reporting of minor problems or other conditions, which may not per se be problems warranting immediate action, but may be symptoms of more significant problems that already exist or may occur. The system may analyze the reports to detect current or predict future, more significant problems. Results of the analysis may trigger output, such as an alert, when a detected or predicted problem is classified with a significance above a threshold. Alternatively or additionally, results of the analysis may be used to schedule corrective action, possibly preventing a larger problem from occurring. As yet a further alternative, results of the analysis may be presented as reports that convey information formatted in any one or more ways. These reports may be pushed to users of the system or may be accessed by users via an interactive interface that may be updated as new reports are received and analyzed.

In some embodiments, problem reporting may be facilitated through a distributed user interface to the system. The user interface may enable employees, workers, contractors, customers, patients, or others interacting with the system who may encounter scenarios indicative of a problem to make a report of a condition from a location at or near where the condition was encountered. In some embodiments, the distributed user interface may be implemented through portable electronic devices, such as smart phones, which may be available to many workers inside and outside a facility who may report problems.

In some embodiments, reporting of conditions that may signify a problem may be promoted by providing a simple user interface through which a worker may quickly provide information about a scenario. A simple user interface may be implemented by, at any time, providing to a worker a relatively small and finite number of choices of conditions to report. Choices may be presented in layers, each with a small number of choices. A choice may be made by the worker by simple user interface techniques, such as clicking or touching an item from a menu presenting the choices. Moreover, the choices presented at a second time may be altered by a choice made by a worker at a prior, first time. In some embodiments, the choices presented to the worker may be selected or otherwise limited based on contextual information.

Further, in some embodiments, the user interface may facilitate input relating to conditions in other ways. In some embodiments, one or more of choices may include attaching a video file, audio file, image file, other multimedia file, geotag, timestamp, or other situational data file or tag, or otherwise sending situational data, thereby providing data-rich, high-sample rate, real-time reporting. In some embodiments, sending supporting documents, illustrations, animations, video, audio, video chat to the front-end user may be supported.

In some embodiments, reports of conditions may be provided to a physical, or electronic, backend location at which analysis is performed. At the backend location, reports from multiple individuals may be aggregated and analyzed. The analysis may include any one or more operations, including validating reports, performing trend analysis or correlating multiple reports.

In some embodiments, the information provided by the reporting system may be directed to one, or multiple, recipients for review or for triggering one or more responses. In some embodiments, immediate response may be enabled for sending supporting information to the reporting worker or other individual at the problem location. In some embodiments, the reports may be aggregated to provide an overview of emergent problems within the organization or may highlight locations where process changes are warranted, have been effective or ineffective or otherwise provide information useful in managing the organization. By aggregating the reports in real time, the system may automatically identify hot spots at which urgent attention to a problem may be warranted and/or quiescent areas for which response may not be warranted. Aggregation may occur by location, by trend, by concentration, by problem type, or by other criteria.

According to an aspect of the present application a communication system for processing problem reports within an organization, wherein problems may be encountered by workers and may be addressed by one or more support personnel is provided. The system comprises a communication interface, wherein the communication interface is configured to receive reports from portable computing devices used by the workers, and the reports are based on selections made through a menu-based interface through which a user may specify at least a problem type and a severity. The system further comprises a computer readable storage media storing a mapping from a problem type and a severity to support personnel. The system further comprises a server configured to process reports received through the communication interface, wherein the processing comprises, for each report of at least a portion of the reports identifying at least one support person as a recipient of information contained in the report based on the mapping and transmitting information derived from the reports to a computing device associated with the identified support person.

According to an aspect of the present application at least one computer-readable storage medium storing computer-executable instructions that, when executed by a processor, perform a method of reporting a problem within an organization by analyzing user input provided by a worker encountering the problem through a user interface of at least one computing device, wherein the user interface is configured to present a plurality of choices indicating possible conditions to report is provided. The method comprises identifying a first set of choices from among the plurality of choices to present on the user interface based on contextual information, identifying a second set of choices from among the plurality of choices to present on the user interface based on user input indicating selection of a first choice from among the first set of choices, wherein the second set of choices includes conditions within a category constrained by the condition identified by the first choice, and generating a report constructed from information provided by the first choice and a second choice selected from among the second set of choices by user input.

According to an aspect of the present application a method of reporting a problem encountered by a worker to at least one support person of an organization by analyzing a user input provided by the worker to a user interface associated with at least one computing device is provided. The method comprises identifying a plurality of choices that indicate possible conditions of different types of problems, wherein the plurality of choices is organized in hierarchical layers based on contextual information associated with the organization. The method further comprises presenting, by the user interface, the plurality of choices by presenting choices corresponding to one hierarchical layer at a time. The method further comprises receiving, from the worker, user input indicating selection of a portion of choices from the plurality of choices such that the selected portion of choices are from different hierarchical layers. The method further comprises constructing a report indicating conditions based on the selected portion of choices and transmitting the report to at least one second computing device associated with at least one manager identified as a recipient for the report.

According to an aspect of the present application a portable electronic device is provided. The portable electronic device comprises a display configured to display a menu-based interface and control circuitry configured to perform a method comprising identifying a first set of choices from among a plurality of choices based on contextual information, wherein the plurality of choices indicates conditions of problems and is organized in hierarchical layers, and the first set of choices is associated with a first layer of the hierarchical layers, presenting the first set of choices as menu options on the menu-based interface, receiving, from a worker, user input indicating selection of a first choice from among the first set of choices, and identifying a second set of choices from among the plurality of choices based on the selected first choice, wherein the second set of choices is associated with a second layer of the hierarchical layers constrained by the selected first choice.

The foregoing is a non-limiting summary of the invention, which is defined solely by the attached claims.

BRIEF DESCRIPTION OF THE DRAWINGS

FIGS. 4-10 illustrate a user interface for use in a problem reporting system, in accordance with some embodiments.

FIGS. 11-20 illustrate a further user interface for use in a problem reporting system, in accordance with further embodiments.

DETAILED DESCRIPTION

Figure 1:
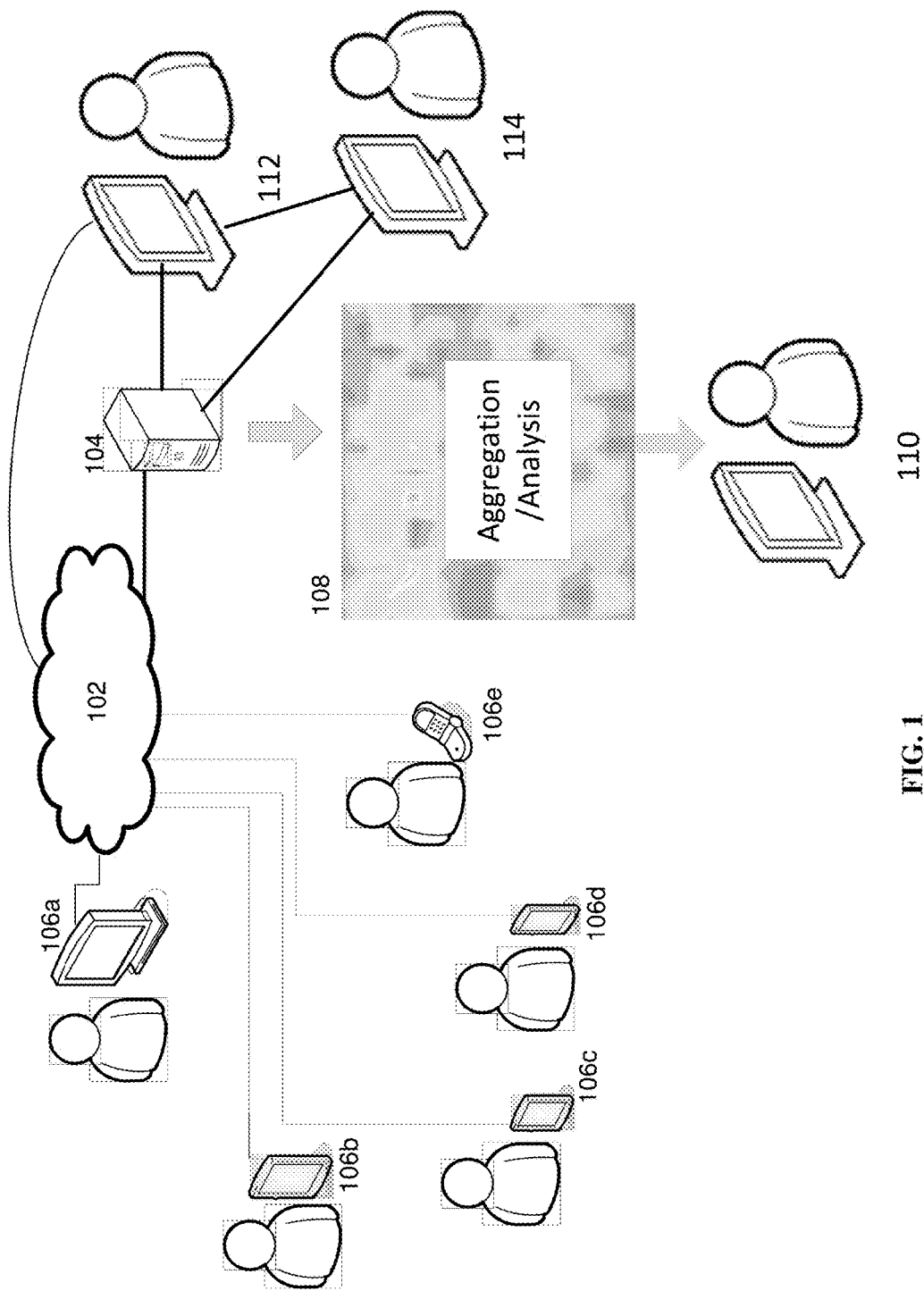
FIG. 1 is a conceptual diagram of a system illustrating a distributed problem reporting system, in accordance with some embodiments.

The inventor has recognized and appreciated that an organization may be better managed, with fewer problems, and at lower cost through the use of a distributed problem reporting system that reduces the burden on a worker of making problem reports. Problems encountered by workers may be addressed by one or more support personnel including technical support people with skills to aid in resolving the problem and/or managers who may oversee and monitor workflow tasks within the organization. Some organizations may include multiple levels of support personnel, and identifying a recipient for a report may include identifying a level of support within the organization as an intended recipient of the report. In accordance with some embodiments, a distributed problem reporting system may, based on present and/or past problem reports may determine the appropriate routing of problem reports within the organization.

As a result of reducing the burden of making reports, workers may make more problem reports and may report conditions of lower severity. Though low severity conditions may not warrant immediate action, rather than overwhelm the system with non-actionable information, these low severity problems may be aggregated and analyzed to identify the existence of larger problems that presently exist or may indicate conditions that might turn into problems that can be foreclosed with maintenance. The system may perform analytics on the problem reports to aid a management user in scheduling maintenance to address current and potential problems. Such a solution may be useful in the problem domains of healthcare, manufacturing, natural resource extraction, and administrative work, among others.

Although all complex systems may have problems, these problems can be most effectively contained and solved when information regarding the problems is made available while that information is current and relevant to the problem. In some instances, the way a problem is reported may affect steps taken to address and/or resolve the problem. When a report is made soon or near to where the problem occurs, then resolution of problem may be quick, effective. While delayed problem reporting or reporting a problem to support personnel at a location far from where the problem occurs may reduce effectiveness in resolving the problem. The inventor has also recognized and appreciated that providing information at an early stage allows for managers to be proactive in solving potential problems before they become emergencies. Accordingly, problem reports may be collected in real-time through a distributed interface that makes reporting tools available to workers where they may encounter conditions that warrant a report.

Moreover, the reporting tools may be provided with a simple user interface that makes reporting of a problem very simple. If the burden on a worker of reporting a problem is low, in some scenarios less than working around the problem without reporting it, the percentage of scenarios indicative of a problem for which a report is generated in real-time may increase. For example, in a hospital setting, if a healthcare worker needs to use a piece of equipment to perform a medical procedure, but finds an improperly sterilized piece of equipment in the room where the procedure was to be performed, the worker may take another properly sterilized piece of equipment from another room. The worker may not take the time to fill out a form reporting the problem or track down a supervisor, as these actions would likely prevent the worker from completing the procedure in a timely way. However, using a distributed reporting system with a very simple user interface, the worker may have access to a simple interface to the problem reporting system and can make a report of the problem in a way that does not interfere with the procedure.

Even if the worker might have filled out a report form following completion of the procedure, such a report does not provide real-time information that can provide an early warning of needed attention. For example, the unsterilized piece of equipment may be a symptom of a problem in a sterilization facility, such as might be caused by an improperly trained worker. Getting a report in real-time may provide early warning of a potential more serious problem, for example the more serious problems that might occur if other workers do not recognize that the equipment is not being properly sterilized and use the equipment anyway. Obtaining early-warning actionable information prevents managers from having to deal with problems in a contain-and-cleanup mode, and is more efficient than dealing with a full-scale emergency. Accordingly, the inventor has developed systems and methods for conveniently and non-disruptively capturing useful information and for analyzing it in aggregate to identify current and potential problems or otherwise provide useful management information to an organization.

The systems and methods presented herein provide a solution to the problem of disruptive reporting in the field. When reporting is disruptive to a task being performed, the worker is forced to choose between reporting and completing the task, leading to persistent, unavoidable underreporting and stale data. These issues in turn make it difficult for management to identify problems, as the underlying data may be missing (e.g., underreporting) or out of date (e.g., stale). A problem left unidentified may become larger and more difficult to contain, so that when it is discovered, addressing the problem requires far more effort and cost than if it had been discovered earlier on.

One way to reduce the difficulty of reporting is to enable reporting from a portable computing device, which enables a user to make a report without requiring the user to go to a fixed console to enter a report. For example, in the healthcare example referred to above, a nurse may be able to treat a patient while also reporting a problem with equipment. The portable computing device may be a smartphone or similar device. Alternatively or additionally, the device may be a tablet or similar computing device that a worker may carry for other reasons as part of their work. As yet a further possible alternative, the report-receiving device may be a dedicated device. The use of portable or mobile devices to report problems allows problems to be called out unobtrusively at the location of the problem in the flow of work, instead of forcing a user to go to a dedicated console in an inconvenient location to report the problem.

However, it should be appreciated that it is not necessary for the user interface to be implemented using portable electronic devices. In some embodiments, a heterogeneous selection of portable and fixed electronic devices may be supported for use by various worker users, or by the same user, or both.

Another way to reduce the difficulty of reporting is to use available information about the situation without requiring a user to specifically input that information. Using a smartphone, such as an Apple iPhone™ or Google Android™ device, data regarding the present situation from a number of sensors may be available. For example, a global positioning system (GPS) sensor may allow the user's location to be automatically submitted in a report without requiring the user to enter the location manually. Mobile devices may include cameras, microphones, inertial sensors, radio receivers and possibly other components that may be used in recording time, place, and situation, which provide context information about the problem being reported and which provide a data-rich problem report. A portable computing device may identify a particular worker associated with the device and/or using the device, such as through a device ID, phone number, or password code specific to the worker. In some embodiments, identification of a recipient for the report may include analyzing the context information to determine a support person suitable for responding to the problem having the specific context information. Selection of a support person to receive the report may include determining, based on context information, support people responsible for a particular location, time, situation, and/or type of problem provided.

Another way to reduce the difficulty of reporting is to reduce the time required to submit a report. Shortening the required time allows the reporting to be performed without disrupting the performance of a task at hand. In some embodiments, reporting may be performed in as few as ten or fifteen seconds.

A significant reduction in time, in many cases, may be obtained by reducing the degree of interaction required for the worker-user to submit a report. Free text entry requires a high degree of interaction. When free text entry is lessened or eliminated, interaction is reduced and the time required to make a report is reduced. In order to reduce free text entry, information must be entered using other means, such as selecting from a pick list or menu, selecting from only a finite list of items, selecting from a list that has been constrained by the situation, etc. A menu-based user interface may present choices for a worker to select, and the selected choices may be used to construct a report. The choices may indicate possible conditions or different types of problems that a worker may encounter. The choices may specify a problem type and/or a severity of a problem. The items presented on the menu-based interface to a user may be dynamically selected based on context information. The context information may include prior pick list items selected by the user, location, user job function or any other available information.

Identification of support personnel as a recipient of a report generated from selections made by a worker through a menu-based interface may include mapping the selections to the support personnel. Support personnel may be identified by the combination of selections made by a worker through a menu-based interface. A predetermined mapping of selections to support personnel may allow of the system to identify certain support personnel based on the combination of selections made by the worker.

In some embodiments, the mapping may include relating a problem type and/or a severity to support personnel. For example, a problem of low severity may be mapped to first level support person, while a problem of higher severity may be mapped to a manager. The severity associated with a problem report may be from worker input in a system in which a worker may specify the problem type and/or the severity as selections within the menu-based interface. Alternatively or additionally the severity may be derived from problem reports and other context information. For example, severity may increase if a problem is not indicated to have been resolved after a period of time or if multiple reports of the same problem are received.

The mapping may be stored in a computer readable storage medium and accessed by a processor of the system to identify one or more support people as recipients of a report based on the mapping. The mapping may be customized for an institution using the problem reporting system. The problem reporting system, for example, may provide a user interface through which an administrative user may specify the mapping. Such a user may generate the mapping based on workflow management structure within an organization.

Though input may be received through interfaces in any suitable format, elimination of free text entry also improves aggregation and/or routing of problem reports. Limiting input choices may provide a built-in characterization of inputs, and avoids the need for processing to categorize free text. Limiting choices also may avoid the need for data cleaning to address inaccuracies or subjective comments in free text that can be problematic for extracting meaning. Aggregation of reports may occur based on menu-based interface selections made by a worker used to construct each report. Reports may be aggregated based on one or more conditions indicated by the selections. Reports may be aggregated if a particular selection was made in constructing the reports. In some embodiments, aggregation of multiple reports may allow for identification of a problem and/or a severity. Aggregation of the reports may identify a problem that may not be indicated by an individual report. For example, reports having a low severity level may be aggregated by identifying reports with one or more selection indicating a low severity level, and the aggregated reports may identify a systemic problem within an organization. Continued aggregation of reports may allow for monitoring of the systemic problem over time, providing support personnel with a metric indicating a degree of the systemic problem. In some embodiments, aggregation or reports may include identifying a subset of reports based on contextual information such that each report among the subset of reports relates to similar contextual information. Higher level support personnel, such as second-level support personnel and managers, may receive aggregated reports. A higher level support person may be identified based on information from the aggregated report, including the problem and/or severity identified based on the aggregated report.

As with other characteristics of the illustrated embodiment, ease of use may be prioritized in order to reduce the amount of time and energy required to submit a problem report. The ease of use, rapid reporting time, and simplicity of a reporting application may be designed to make reporting less painful than ignoring the problem or walking away, and may allow a user to both perform his or her originally-intended goal (e.g., treating a patient in a medical context) and to report the problem as well.

Even if no free text entry is supported, free form information can still be sent along with the report by using images, video, sound recordings, and other types of multimedia. Modern smartphones and other portable electronic devices are equipped with cameras, and enable information to be reported naturally, in a contextually-appropriate manner, and with high information density. A photograph or video recording can also provide a common point of reference for use by support personnel in subsequent interactions with the user. A worker reporting a problem may include information in addition to selections made through a menu-based interface, such as an image of a scene and/or a sound recording of the worker communicating details about the problem. This information may improve facilitation of resolving the problem by providing the support personnel with additional information.

In some embodiments, one-way or two-way communication may also be enabled using a smartphone or other portable electronic device in communication with the backend of the problem reporting system. For example, a two-way communication facility may be useful particularly for a user who has just reported an urgent issue and needs to communicate further details to the reportee, or for a user who needs help or information from the reportee. Support personnel may respond to a worker's report submission by providing instructions indicating corrective actions that may resolve the problem. The instruction may be in any suitable form including a text message, document, image, weblink, audio and/or video. In some embodiments, two-way communication may allow the support personnel to directly communicate with the worker in real-time such as through the use of audio and/or audio-visual communication techniques.

Reducing the difficulty of reporting in this manner enables timely and frequent reporting of issues. Such real-time reporting makes more data available for use by management to analyze. In some embodiments, a management system may use these reports to infer correlations, identify problem areas or specific problems that currently exist, and/or predict problems that have not yet arisen. As well, in some embodiments, the backend management system may provide aggregation and analytics to enable managers to review the reported data effectively.

A distributed problem reporting system may be implemented using any suitable devices. FIG. 1 illustrates an exemplary embodiment of a distributed problem reporting system implemented using multiple computerized devices. The problem reporting system may be used by an organization, such as a hospital or company. In such an embodiment, the multiple computerized devices may be distributed throughout locations at which workers for that organization performed tasks. The computerized devices may be distributed by being installed in fixed locations or may be distributed as a result of being portable and carried by workers as they move throughout facilities of the organization.

FIG. 1 illustrates both fixed and portable electronic devices providing interfaces to a problem reporting system. Computer 106A, for example, may be a computer installed at a fixed location at which conditions indicating a problem may be observed by a worker. In this example, a worker in the vicinity of computer 106A may enter a problem report through a user interface presented on computer 106A. Such a user interface may be implemented using known computer programming techniques.

Portable electronic devices also may be programmed to provide interfaces for workers to enter problem reports. Portable electronic devices may be devices that workers carry or access while performing tasks associated with their work. Device 106B for example, may be a tablet. Devices 106C and 106D, for example, may be smart phones. Device 106E, for example, may be a non-smart phone, that may communicate problem reports using techniques such as voice, a voice recognition gateway, or interactive voice response system in which keys provide responses to voice prompts. Moreover, because the user interface described herein may be implemented by offering a worker-user a finite number of options at one time, in some embodiments, a phone with even a simple user interface may be configured to enable the user to enter problem reports.

In the illustrated example, the computerized devices are interconnected by a network 102. Network 102 may be any suitable public or private network. Network 102, for example, may be the Internet. However, in the embodiment illustrated in FIG. 1, network 102 is a private network such as may be found in a hospital such that communications sent over network 102 may be encrypted or otherwise secure.

Moreover, it should be appreciated that network 102 may represent a combination of networks operated by different entities. For example, some problem reports may be sent over a private network from a computer hardwired to that network. Other problem reports may be sent wirelessly, such as over a cellular telephone network. Accordingly, it should be appreciated that the specific type of network used to communicate problem reports is not critical to the invention.

Using network 102, 106A . . . 106E, through which problem reports are entered by workers, problem reports may be passed to other computerized devices for processing at a system backend. The system backend may include a communication interface configured to receive reports from one or more portable computing devices used by workers. In the example in FIG. 1, server 104 may perform data processing to aggregate problem reports and/or perform analysis on the problem reports.

In the example of FIG. 1, server 104 acts as a backend server for the problem reporting system. Server 104 may be coupled to network 102 and may receive problem reports over the network. Server 104 may store the problem reports in a database or other suitable hardware component. Server 104 may identify a recipient of one or more problem reports based on information contained in the one or more reports and transmit information derived from the reports to a computing device associated with the identified support person.

Server 104 may use a mapping to identify support personnel as recipients based on the selections made by a worker and/or other suitable information. In this manner, the selections provide both information reporting conditions of a problem and information used to identify a recipient for the information. Information contained in the report may include a problem type and a severity, and a support person may be identified based on a mapping that identifies support personnel based on reported problem type and/or severity.

The mapping may be based on any suitable type of information. For example, configuration of the mapping may include aspects of organizational levels within an organization such that reported problems of a certain type are sent to a person within a suitable support level. Identification of a support person may include identifying a level of support within the organization suitable for responding to an identified problem and selecting a support person within the level of support. The mapping may identify a specific person associated with each level of support or with each class of problem within a level of support. Alternatively or additionally, the mapping may identify multiple people within a level of support and the system may select one such person to receive a problem report. The selection may be random or may be based on other dynamic criteria, such as workload or current location of the support personnel.

The mapping may be stored in server 104 and/or accessed by server 104 through a communication interface such as network 102. The backend may include a transmitter to transmit the information derived from one or more reports to a computing device 112 associated with the identified support personnel. Computing device 112 may communicate to one or more devices associated with workers over network 102. In this manner, support personnel may provide direct communication and instructions to individual workers.

Higher level support personnel may monitor the activity of problem reports and responses provided by recipients of the reports. Monitoring this activity may allow for identification of problems within an organization in its ability to resolve problems. In FIG. 1, device 114 is associated a second level support person who may be responsible for overseeing the work performed by support person associated with device 112. Device 114 may receive reports from server 104 and response activity provided by support person associated with device 112. Response activity may include information related to the ability of the support person to respond to a report including the time to respond to a report, the types of reports received, and/or the types of instructions provided to the workers generating the report. Though FIG. 1 shows a direct connection between devices 112 and 114, it should be appreciated that such communication may be achieved by back and forth communication between device 112 and server 104 and device 114 and server 104.

Identification of recipients of reports by server 104 may be identified by the mapping. The mapping may include determining a lower support person recipient for a report and identifying a second level support person for the report based on the lower support person.

Alternatively or additionally, server 104 may perform aggregation and analysis functions 108. The output of analysis and aggregation functions 108 may be presented on another computerized device. In this example, the output of the aggregation and analysis functions 108 is presented on computer 110.

Computer 110 may provide a user interface through which the results of the analysis may be accessed by a service manager or other person associated with the organization that uses or responds to information about problems. The output may be presented in any suitable format. In some embodiments, output resulting from the analysis problem reports may be on alert of a current problem requiring attention. In some scenarios, the result of analysis may be an indication of maintenance tasks that may avoid future problems. In other scenarios and/or in other embodiments, the output may represent statistical information about the reporting or the nature of the problems. Such information, for example, may be accessed by an administrator in the organization to make management decisions, such as publication of staffing and resources.

Any suitable aggregation and analysis functions may be performed. For example, server 104 may aggregate problem reports that likely relate to the same scenario. Alternatively or additionally, server 104 may aggregate problem reports relating to different symptoms of the same problem. Aggregation may be performed in any suitable weighting, such as by type of problem report or location problem report or location of the conditions reported.

The raw problem reports and/or aggregated data derived from a problem reports may be analyzed in any suitable way.

The analysis, for example, may identify a type and/or location of a problem that would likely have given rise to observed problem reports. Such analysis may be performed in any suitable way, including using rules or other heuristics, trained classifiers or other suitable data analysis techniques.

Figure 2:
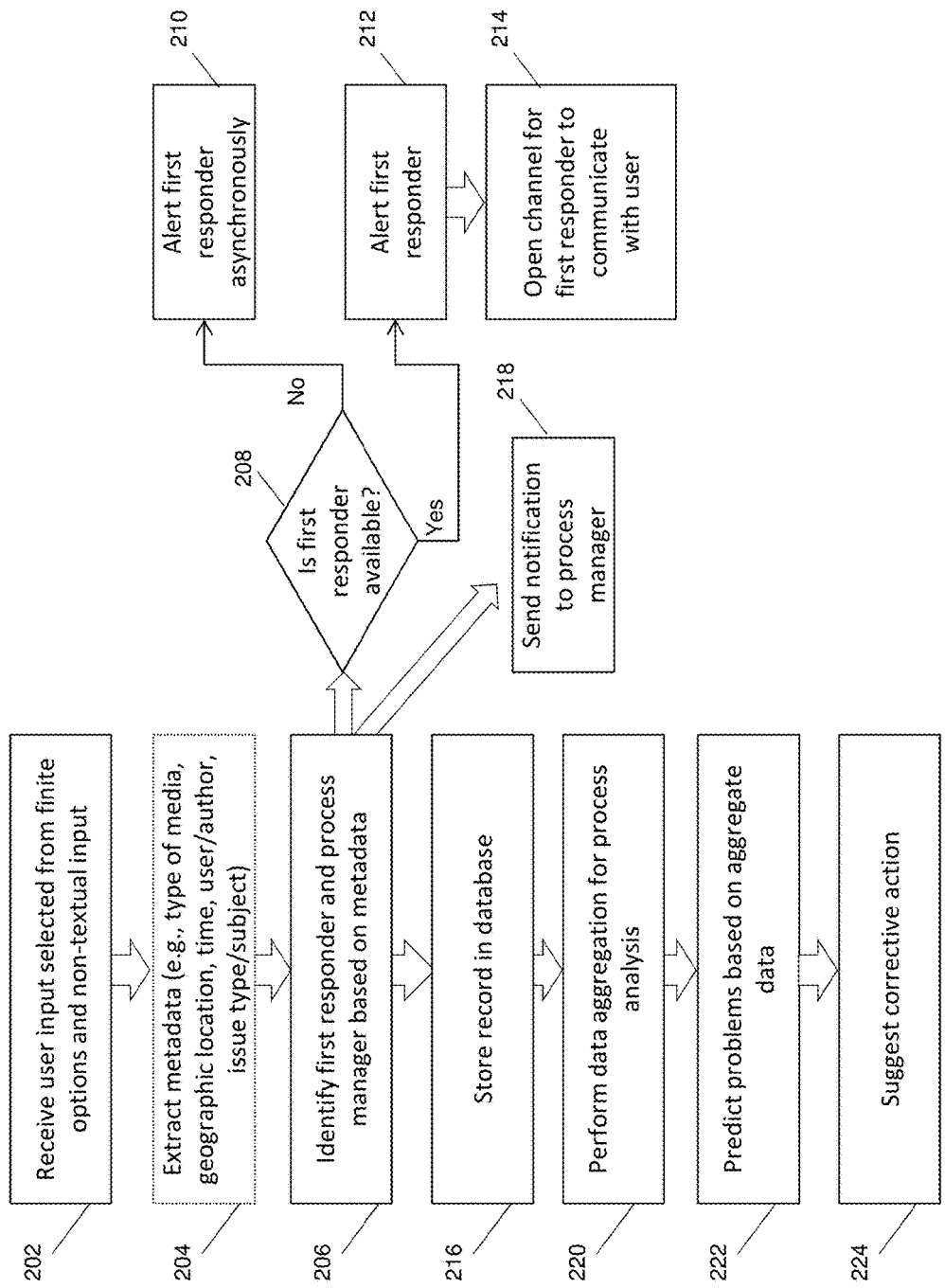
FIG. 2 is a flowchart of a method for problem reporting and identification, in accordance with some embodiments.

The distributed user interface of the problem reporting system illustrated in FIG. 1 the name of the collection of information that aides in response to problems and better management of an organization. FIG. 2 illustrates a method of operation of an organization using the problem reporting system, such as illustrated in FIG. 1. The processing illustrated in FIG. 2 may be performed by a computing device, such as server 104, or any other suitable device.

The method of FIG. 2 begins at step 202 at which user input is received. Such input, for example, may be received through a user interface implemented by programming on a mobile device, such as devices 106B . . . 106E, in the embodiment of FIG. 1. This input may be in the form of a selection or combination of selections from one or more menus or pick lists formatted in any other suitable way including a menu-based interface. The user interface may have multiple layers such that a user may drill down to select an appropriate entry from among more choices that may be presented on the user interface at one time.

The user interface may present a plurality of choices indicating possible conditions to report by identifying a first set of choices based on contextual information and identifying a second set of choices based on user input indicating selection of a first choice from among the first set of choices. The second set of choices may define a category constrained by a condition identified by the first choice. In this manner, a worker may make selections among multiple layers of choices. Choices presented to a worker may be organized in hierarchical layers where the choices within each layer are based on information associated with an organization including management workflow structure, types of problems encountered by workers, and types of work performed by workers. Moreover, the user interface may have multiple parallel branches such that a user may supply multiple types of information by traversing different branches of the user interface.

Further, the user interface may exempt information about the scenario in non-textual form. The input, for example, may constitute a photograph, video, or a sound recording. Alternatively, non-textual input may be obtained through speech recognition. However, it should be appreciated that, in some embodiments or in some scenarios, input provided as text typed through a keyboard may also be received.

At block 204, the problem report may be processed to extract metadata, such as type of media on which non-textual input was provided, a location from which a problem report was sent, the time, the author of the problem report and other information, such as a type of issue being reported or the subject of the report. In some embodiments, this information may be obtained from the information input by the worker reporting the problem. The issue type and subject, for example, may be identified from information input by the worker. That information, for example, may indicate the severity of the problem reflected in the report. Other information may be obtained automatically. For example, a geographic location which the report was sent may be obtained from GPS hardware in the portable device from which the report was sent. Likewise the type of media in which non-textual input was provided may be obtained by analyzing a file containing that media transmit the report.

Processing of reports may include identifying a type of response based on the severity and the identified problem. At block 206, the report may be analyzed to determine whether the severity is such that a response is currently required. Some problems, for example, may require a response, such as dispatching maintenance personnel to clean or repair equipment. Other problems, for example, may require user responds that a manager be dispatched to investigate. Yet other reports may indicate the possibility of future work to address. For example, an indication that supplies are being consumed faster than expected may not warrant a current response, but may warrant a process change.

If a current response is required, processing may proceed to decision block 208. At block 208, processing may branch depending on whether a person or other resource to address the problem is available. If such a first responder is available, processing may branch to block 212, where the first responder is alerted. An alert may be sent in any suitable way, such as by an electronic message. Regardless of how the first responder is alerted, the system may also establish a real-time communication channel between the first responder and the worker reporting the problem, as in block 214. In embodiments in which the worker reports problems through a user interface implemented on a smart phone, that communication channel may use audio or video communication channel provided on the smart phone. However, it should be appreciated that any suitable way may be used to form a communication channel. Through such a communication channel, a worker may provide additional information about conditions at a location to aid in problem identification or planning a response.

Conversely, if the first responder is not available at the time the problem report is received, processing may branch from decision block 208 to block 210. At block 210, the report may be provided to the first responder asynchronously such that the first responder may receive the report when the first responder is next available to respond to it. Any suitable way may be used to provide a problem report asynchronously. For example, the server may queue the message until the first responder is available and then deliver it electronically or in any other suitable way. Alternatively, the system may update a schedule of tasks for the first responder, showing response to the problem report as a future task. A visit for a first responder and/or support person suitable for responding to an identified problem may be scheduled based on the severity and/or the identified problem.

Alternatively or additionally, problem reports may signify a need for adjustment to a process. Accordingly, problem reports may be routed to a process manager and/or a second-level support person at block 218. The process manager may be notified of the problem report in any suitable way, including via electronic messages. With this information, the process manager may take corrective action. For example, if the problem report indicates improperly sterilized equipment, a first responder may be a technician that could sterilize the equipment. A process manager may be a manager and/or second-level support person responsible for overseeing the sterilization facility. The process manager may respond to a problem report by providing additional training to workers in the sterilization facility will provide additional staffing.

In some scenarios, a single problem report may provide sufficient identification of a problem to alert a first responder or provide useful information to a process manager. In other embodiments or other scenarios, aggregated problem reports may provide more useful information. Instead of, or in addition to, notifying a first responder and a process manager, processing may proceed to block 216. At block 216 the problem report may be stored in a database.

Storing problem reports in a database may allow data aggregation for process analysis at block 220. Aggregation and analysis may be performed in any suitable way, including as described above.

In some embodiments or scenarios, a result of analysis may be an identification of a current problem warranting corrective action. In that scenario, the problem reporting system may respond as described above in connection with block 206 where a problem is identified from a single report. Alternately or additionally, aggregation and analysis may yield information indicating a scenario likely to lead to a problem. Accordingly, processing at block 222 may entail predicting that a problem may occur without corrective maintenance or other action.

Processing at block 222 may be performed in any suitable way. For example heuristics or rules may be programmed into a server. Alternatively or additionally, one or more machine learning techniques may be used to develop tools, such as classifiers or vector support machines, that can identify conditions that, with a probability exceeding a detection threshold, are correlated with a problem occurring. However, it should be appreciated that any suitable way to predict a problem may be used.

When a problem is predicted, corrective action may be suggested at block 224. Corrective action may be suggested in any suitable way. For example corrective action may be suggested in an electronic message to a maintenance worker or may be suggested by modifying a schedule of maintenance activities to include the corrective action in that schedule. Moreover, it is not a requirement that corrective action be pushed to a manager or other user of the problem reporting system. In some embodiments, such a user may log into the system and access user interfaces through which problem reports, whether in raw form or after having been aggregated and analyzed, may be accessed. Through such interfaces, the user may also review suggested corrective actions.

Figure 3:
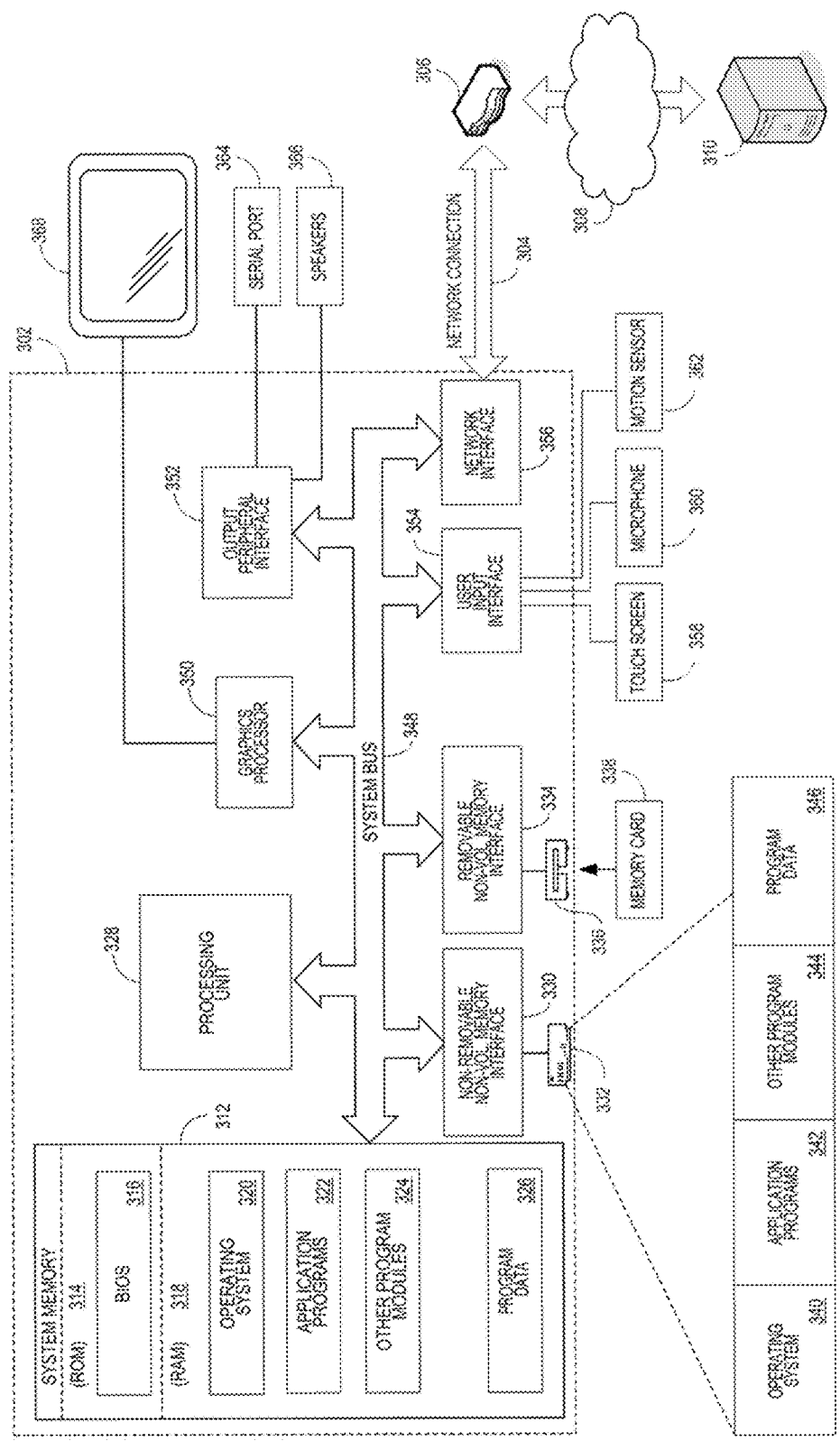
FIG. 3 is a system diagram illustrating a computing device, in accordance with some embodiments.

Processing as illustrated in FIG. 2 may be performed in any one or more suitable computing devices. FIG. 3 illustrates exemplary components of a suitable computing device. Similar components may be included in computing devices implementing a distributed interface to the problem reporting system.

FIG. 3 illustrates an example of a suitable computing system environment on which the invention may be implemented. A computing environment as illustrated may represent a device through which a worker-user interface is provided to receive problem reports and/or may represent a backend server that may perform processing, aggregation, and analysis functions. The illustrated computing system environment is only one example of a suitable computing environment and is not intended to suggest any limitation as to the scope of use or functionality of the invention. Nor should the computing environment be interpreted as having any dependency or requirement relating to any one or combination of components illustrated in the exemplary operating environment.

A problem reporting system as described herein may be operational with numerous other general purpose or special purpose computing system environments or configurations. Examples of well-known computing systems, environments, and/or configurations that may be suitable for use with the invention include, but are not limited to, smartphones, cell phones, tablets, hand-held or laptop devices, multiprocessor systems, personal computers, server computers, microprocessor-based systems, set top boxes, programmable consumer electronics, network PCs, embedded computers, personal digital assistants (PDAs), distributed computing environments that include any of the above systems or devices, and the like.

The computing environment may execute computer-executable instructions, such as program modules. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 3, an exemplary system for implementing the invention includes a general purpose computing device in the form of a computer 302. Components of computer 302 may include, but are not limited to, a processing unit 328, a system memory 314, and a system bus 348 that couples various system components including the system memory to the processing unit 328. The system bus 348 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, PCI-X bus, Advanced Graphics Port (AGP) bus, PCI Express bus, HyperTransport, the Advanced Microcontroller Bus Architecture (AMBA) bus used by ARM Limited, or other bus technology.

Computer 302 may include a variety of computer readable media. Computer readable media can be any available medium that can be accessed by computer 302 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 302. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of the any of the above should also be included within the scope of computer readable media.

The system memory 312 includes computer storage media in the form of volatile and/or nonvolatile memory such as read-only memory (ROM) 314 and random access memory (RAM) 318. A basic input/output system 316 (BIOS), containing the basic routines that help to transfer information between elements within computer 302, such as during start-up, is typically stored in ROM 314. RAM 318 typically contains data and/or program modules that are immediately accessible to and/or presently being operated on by processing unit 328. By way of example, and not limitation, FIG. 3 illustrates operating system 320, application programs 322, other program modules 324, and program data 326.

The computer 302 may also include other removable/non-removable, volatile/nonvolatile computer storage media. By way of example only, FIG. 3 illustrates a non-removable non-volatile memory interface 330, that reads from or writes to a non-removable non-volatile memory 332. The non-removable non-volatile memory 332 may be a flash memory. As well, a removable non-volatile memory interface 334 may be included in computer 302, and may interface with memory card 338 via memory card interface 336. Other removable/non-removable, volatile/nonvolatile computer storage media that can be used in the exemplary operating environment include, but are not limited to, hard drives, network drives, magnetic tape cassettes, flash memory cards, digital versatile disks, digital video tape, solid state RAM, solid state ROM, and the like.

The computer storage media discussed above and illustrated in FIG. 3 provide storage of computer readable instructions, data structures, program modules and other data for the computer 302. In FIG. 3, for example, non-volatile memory 332 is illustrated as storing operating system 320, application programs 322, other program modules 324, and program data 326. Note that these components can either be the same as or different from operating system 320, application programs 322, other program modules 324, and program data 326. Operating system 340, application programs 342, other program modules 344, and program data 346 are given different numbers here to illustrate that, at a minimum, they are different copies.

A user may enter commands and information into the computer 302 through input devices such as touch screen 358, microphone 360, and motion sensor 362. Other input devices (not shown) may include a joystick, game pad, satellite dish, scanner, mouse, trackball or touch pad or the like. Further exemplary input devices may be wireless input devices such as a wireless keyboard, wireless mouse, or other wireless device. Bluetooth or radio frequency (RF), or another wireless technology, may be used for connecting to these peripherals. Further exemplary input devices may include a Global Positioning System (GPS) sensor, GLONASS sensor, or other positioning sensor. These and other input devices are often connected to the processing unit 328 through a user input interface 354 that is coupled to the system bus 348, but may be connected by other interface and bus structures, such as network interface 356, a parallel port, game port or a universal serial bus (USB) interface. Touch screen 358 may also include a video screen 368, or another type of display device may also connected to the system bus 348 via graphics processor 350. In addition to the touch screen, an exemplary computer may also include other peripheral output devices such as speakers 366 and serial port 364, which may be connected through a output peripheral interface 352.

Computer 302 may operate in a networked environment using logical or physical connections to one or more remote computers and/or networks, such as network device 310. The network device 310 may be a personal computer, a server, a router, a network PC, a part of a public network or a private network such as a cable internet provider network or a cell data network, a peer device or other common network node, and typically includes many or all of the elements described above relative to the computer 302, although these elements have not all been illustrated in FIG. 3. The logical connections depicted in FIG. 3 include a network 308, which may be a local area network (LAN) or a wide area network (WAN) 373, but may also include other networks, such as an intranet, a private communications network, or the Internet.

Computer 302 may be connected to one or more networks via network interface 356 and network connection 304, which may be part of computer 302, and via network device 306. The network interface 356 may, in some cases, include a wireless network connection and may, in some cases, include an antenna for communicating with data-based wireless network 308, such as IEEE 802.11a/b/g/n, WiMAX, EDGE, UMTS, 2G, 3G, 4G, LTE, or another network. Network device 306 may be a router, gateway, base station, access point, or other device for providing access to network 308. Network 308 may provide connectivity to other networks. Program modules depicted relative to the computer 302, or portions thereof, may be stored in a remote memory storage device on one or more networks. It will be appreciated that the network connections shown are exemplary and other means of establishing a communications link between the computers may be used.

A computing device as described above may be programmed to present a distributed interface. FIGS. 4-11 illustrate exemplary screens that may form a part of a user interface for problem reporting. The user interface may be simple to promote problem reporting. As illustrated, the user interface presented to a worker-user, such as on a portable electronic device, may present a relatively small number, such as less than 10, options at any one time.

Figures 4, 5:
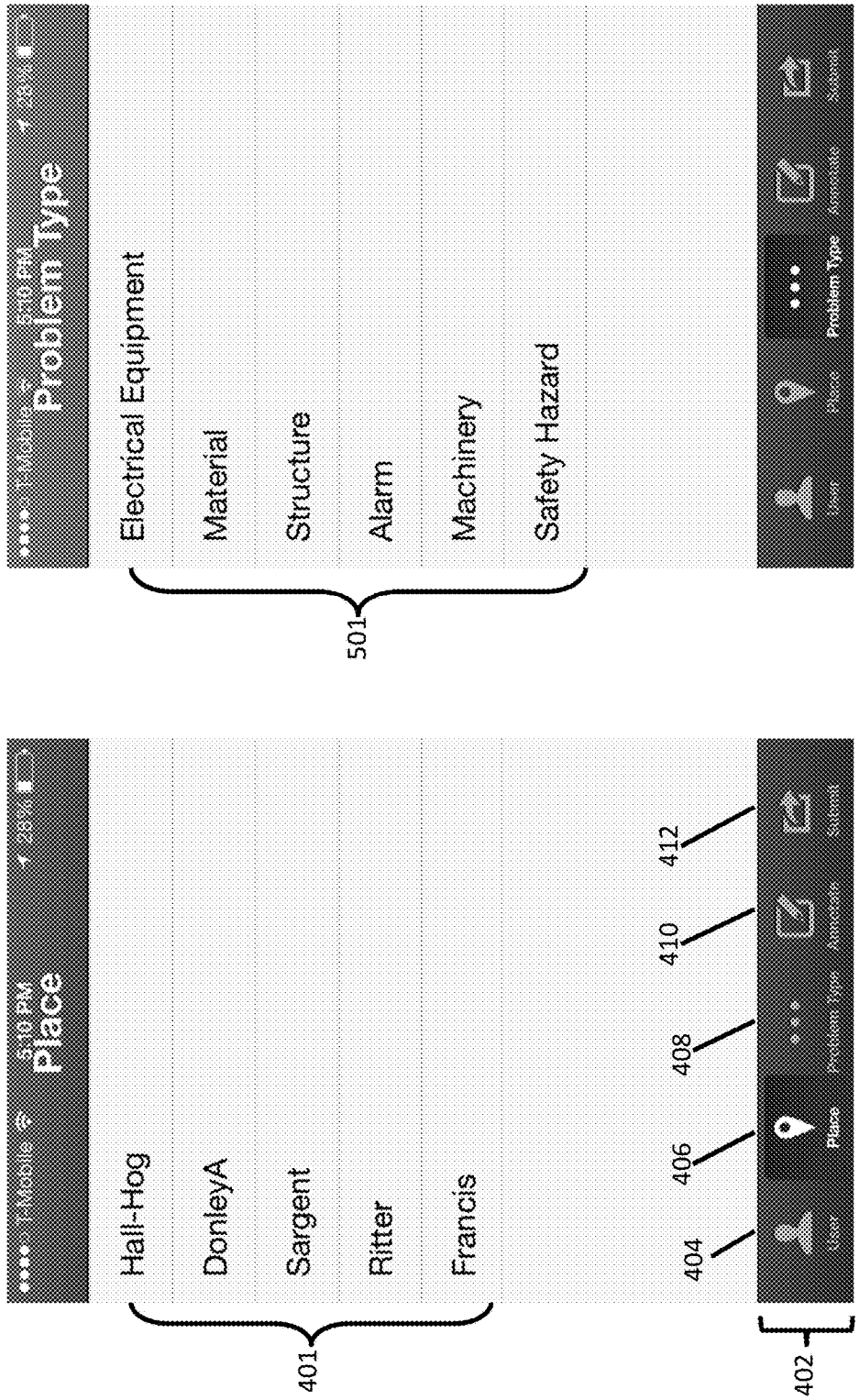

The user interface may include a menu-based interface where a choice selected by a user indicates subsequent choices presented on the interface. FIG. 4 shows a menu bar 402, with a limited number of choices for types of information that a worker may input about a scenario that may indicate a problem. In this embodiment, the menu bar includes menu options providing four choices for types of information that may be provided. These options are: identify user menu option 404, identify place menu option 406, identify problem type menu option 408, and annotate the report menu option 410. A worker, upon encountering a scenario with conditions indicative of a problem, may submit a report by accessing some or all of these menu options. However, because there are a limited number of menu options and selecting each menu option, in turn, brings up a subsequent menu with a limited number of options, a worker may quickly input information needed to complete a report of a problem.

FIG. 4 illustrates the user interface after a user has selected a place menu option 406, according to some embodiments. In the embodiment illustrated, the user interface is implemented on a device having a touch sensitive screen, such that a selection of a menu option is made by the worker touching the screen where an icon associated with a desired option is visible. Such user interfaces may be implemented using known computer programming techniques. However, it should be appreciated that any suitable programming techniques may be used.

In this example, selection of the place menu option brings up a further menu with five choices, represented by pick list 401. Each choice on the list may, in some embodiments, represent a further menu such that selection of a menu option may bring up a further list of choices. For example, each menu option may represent a building or other region. Selection of the region may then bring up a further list, continuing locations within the selected region. This type of drilldown menu structure may be repeated to any desired number of levels, allowing a worker to quickly identify a specific location without text input. A selected choice in one level may constrain choices presented in a subsequent level by the selected choice identifying a category for the choices in the subsequent level. Identifying a second set of choices may include identifying possible second level conditions categorized by a first choice.

The number of items in the list of choices may be configured to ensure that the most relevant choices are presented, either by pre-selecting the choices, or by using algorithms to select which choices are relevant. The number of items on the list may be limited to a set number, such as seven items, or may be allowed to be unbounded. If the number of items on the list exceeds the number of items that can be shown, scrolling can be enabled so that more items may be presented than can appear on a single screen. However, it should be appreciated that in some embodiments, the number of options may be limited so that a worker-user may make a selection based on information visible on the user interface at one time. Accordingly, the pick list may be sized and shaped to allow a user to readily select an item. In the example shown, the items are sized to be selected using a finger on a touch screen.

Context information provided by a worker and/or a device associated with the worker may determine choices to present to the worker. Contextual information may include identification information of the worker, a type of work performed by the worker, a location of the device, a job position of the worker, and/or typical problems encountered. This information may be stored on the device, provided by a sensor of the device, and/or inputted by the worker. As an example, a worker may be identified through an access code for the device where the access code is unique to the worker. By inputting the access code to use the device, the worker and associated context information may be identified. The context information may include prior choices selected by the worker and/or previous type of problems reported by the worker, and identification of the choices to present to the worker on the interface may be based on the context information. As another example, a location of the device may be identified based on a sensor of the device allowing access to the device's GPS location. The location may provide context information related to the work site associated with the location and/or the type of work performed by workers at the location.

Other techniques for identifying context information and/or choices to present to a worker may be used. To facilitate a choice of location, the device presenting the user interface may determine which menu options to present by selecting choices using one or more algorithms. For example, a list of recent places visited by the worker accessing the interface could be presented. Alternatively, a list of places that correspond to known places within an organization, such as wards within a hospital, may be presented. Alternatively, a list of places corresponding to emergent hot spots could be presented, based on analyzing bulk data collected from other users. The list of places may be selected or ordered in various ways, including alphabetically, by proximity to the user's current position using GPS or other technology for geolocation, such as Wi-Fi triangulation, a scannable code at a location or some other form of proximity sensor. Alternatively or additionally, heuristics may be used to limit the number of choices presented to a worker at one time, such as by frequency of interaction with equipment in a location by the worker or other workers, or in other ways.

In other embodiments, the displayed list of choices may be the entire list of choices relevant for problem reporting in a specific context. One or more sources of information may be used to identify the location choices relevant for problem reporting. For example, in some embodiments, GPS data may be used to identify a building or other region in which a worker is located at the time of making a problem report. That information may be used to identify the specific locations within the region to present as menu choices. However, other information alternatively or additionally may be used to identify specific locations for presentation to the worker, such as the worker's role within the organization or locations of prior reports of problems.

FIG. 5 illustrates the user interface after the user has selected identify problem type menu option 408, according to some embodiments. As well as the problem type icon being highlighted, the title of the screen is different to reflect the changed option. A pick list is shown listing problem types. In some embodiments, the list of problem types may be limited to a short list based on the most commonly-encountered problems. In some embodiments, a miscellaneous problem type is provided, to reduce the length of the list of problem types. An alphabetic ordering, or an ordering based on frequency of problem types reported, may be used to order the presentation of the problem types in the pick list.

Figure 6:
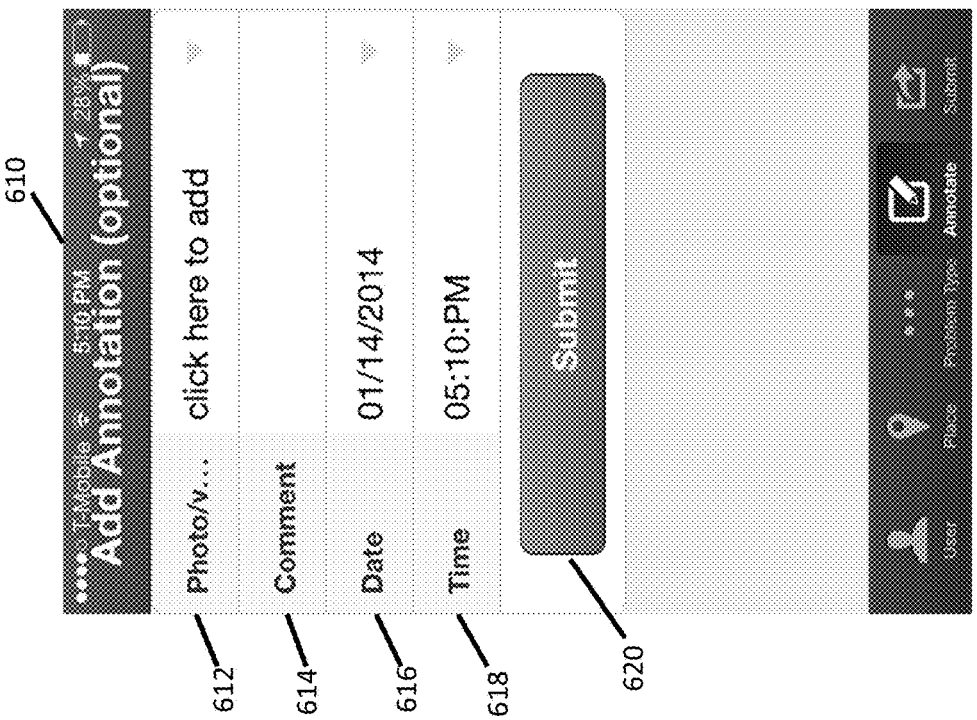

FIG. 6 illustrates the user interface after the user has selected the annotate report menu option 410, according to some embodiments. As described herein, one goal of the present embodiment is to reduce unnecessary interaction, and in particular, to avoid free text entry. For this reason, title 610 may indicate that adding an annotation is optional, in some embodiments. Annotations may include one or more elements, each of which may be optional. Specifically, while a comment field 614 is presented, its use is optional. More commonly, the user may be encouraged to upload a photo or video in photo/video field 612, as a photo or a video allows the reporting user to rapidly convey more information than could be expressed quickly by typing in the Comment field. When no photo or video has been selected, a placeholder phrase may be used to instruct the user, e.g., "click here to add." The date field 616 and the time field 618 may be automatically filled in, in some embodiments. Certain fields, such as a geotag field, may or may not be rendered visually, even if the information may be sent with the problem report. A submit button 620 is provided and configured to allow a user to easily identify and select the button.

Figure 7:

FIG. 7 illustrates the user interface after the user has selected identify problem menu option 404. As in FIG. 4, a pick list is presented to the user, thereby enabling the user to rapidly select his or her own name as the submitting user, or the name of another user who will be submitting the problem report. A scrolling list may be used for the pick list, such that a large number of names may be presented. While keeping the list a short list is advantageous in that it takes less time to submit, scrolling through a long list is still preferable to, and faster than, manual text entry for the name of the submitter, as described elsewhere herein.

Figures 8, 9:
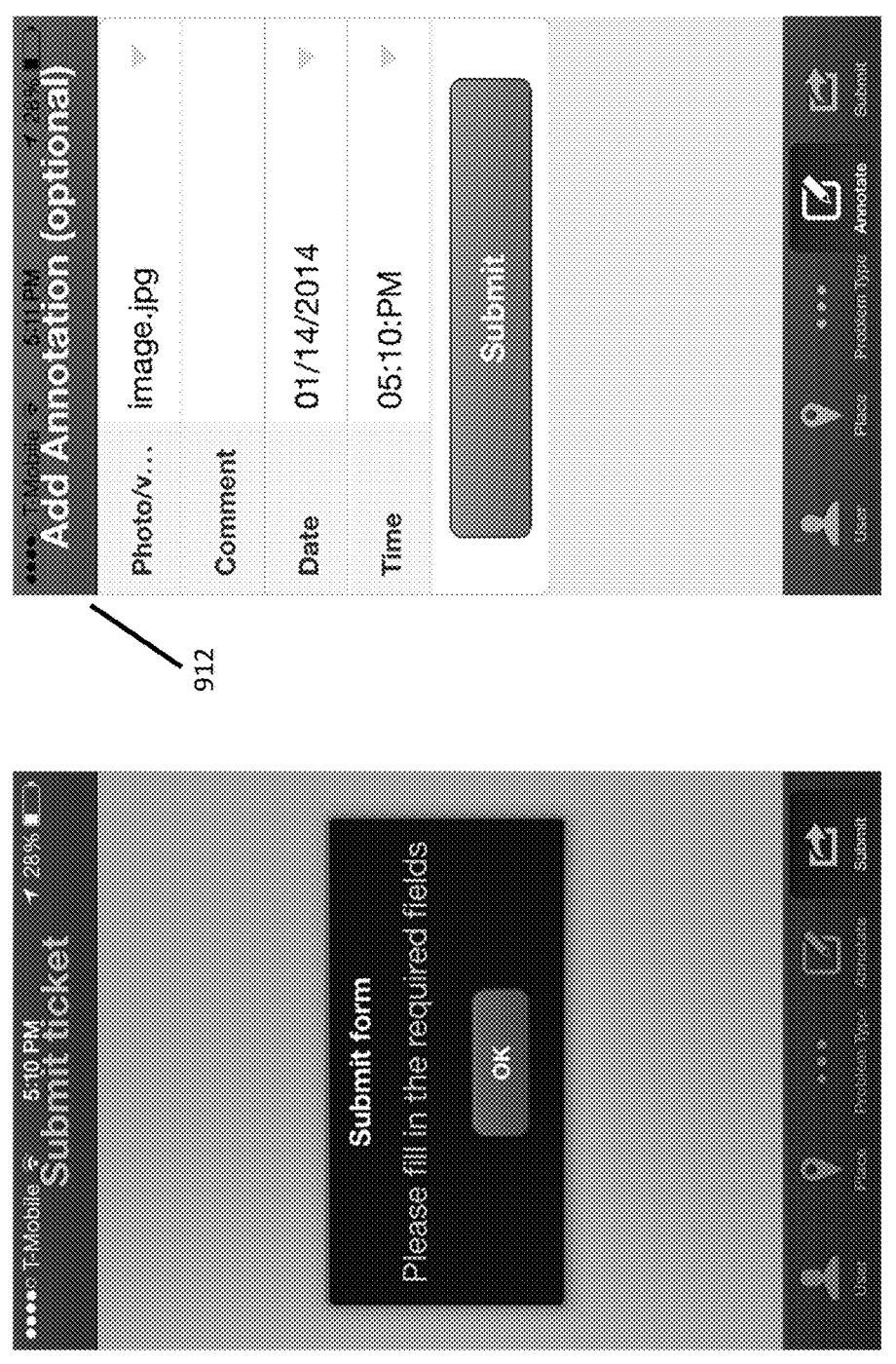

FIG. 8 illustrates the appearance and functionality of a submit error dialog, according to some embodiments. Such a dialog may be presented in response to a report failing error validation performed, either on the device presenting the user interface or backend computer equipment receiving the report. When a user submits a problem report, one or more fields may be required. In some embodiments, it is possible to require no fields, such that maximum flexibility of reporting is achieved. It is unlikely that automatically-populated fields, such as date, time, and GPS location, will be empty, so even if no fields are required, some information about problems is obtained. However, if at least some fields are required to have information or have information meeting predefined criteria for submitting a report, it is more likely that the information will be useful. The application as shown and described relating to these embodiments attempts to reduce the prevalence of such submit error dialogs by making information entry as easy and as rapid as possible.

FIG. 9 illustrates the appearance of photo/video field 612 after a photo has been selected for upload, but before the problem report has been uploaded, according to some embodiments.

Figure 10:
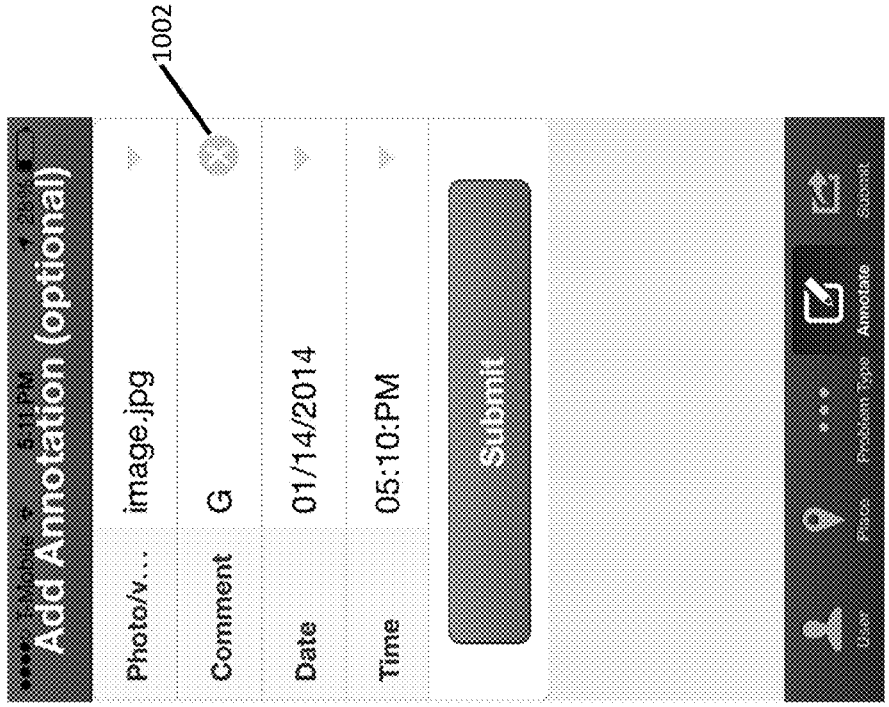

In some embodiments, a user interface may support providing multi-media context information. FIG. 10 illustrates the appearance of photo/video field 612 after a photo has been selected for upload, and after a text comment has been entered, but before the problem report has been uploaded, according to some embodiments. Text comment field 614 has been edited to include a short comment, which is now possible to be cleared using clear control 1002. A short comment may be useful if the comments that are submitted include text that will permit an aggregation system to separate the submitted problem report into one of a plurality of categories. A short comment may also be useful if it contains keywords that an aggregation system may use to identify similarities between reports (i.e., clustering), or when used in conjunction with a semantic analysis system, to identify connections between related problem reports using keywords.

Figure 11:
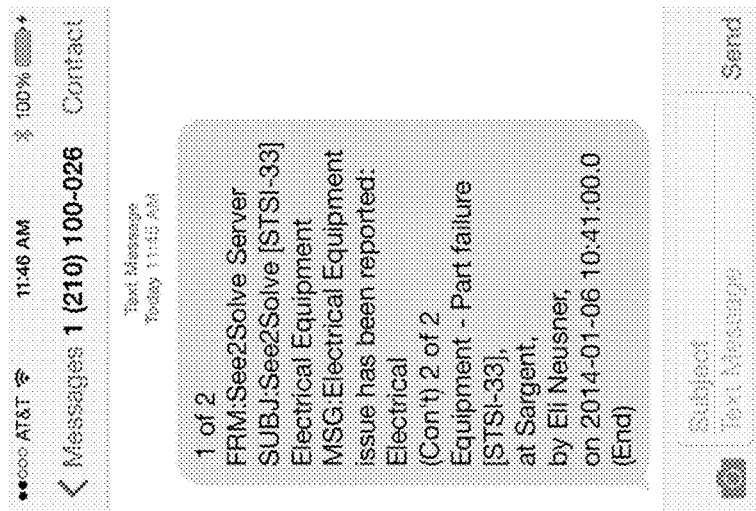

An indicator confirming transmission of the report over a network may be presented to the worker. FIG. 11 illustrates an exemplary confirmation message 1101 being received from a server in response to the receipt of a problem report, according to some embodiments. The confirmation message may include any, all, or none of the information elements submitted in the problem report, in some embodiments. The confirmation message may also include information about how to act on the problem report, or a status report indicating a time estimate for when the problem will be addressed, or other information about how to contact first responders or how to facilitate the resolution of the problem for the end user.

FIGS. 12-19 illustrate an alternative embodiment of a distributed user interface to a problem reporting system. The problem reporting system illustrated in FIGS. 12-19 is configured for collecting problem reports throughout a hospital.

Figure 12:
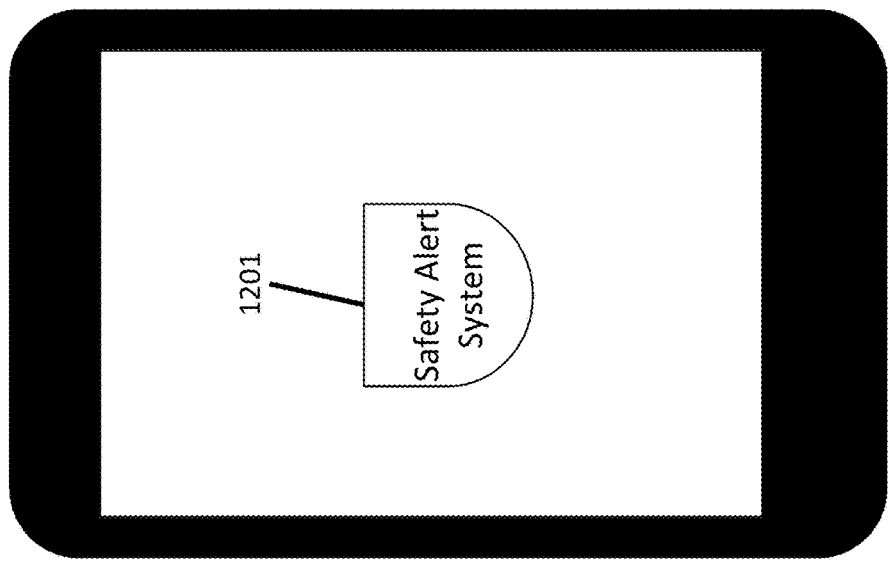

FIG. 12 illustrates a start screen for an application running on a worker's smart phone or other portable electronic device. The application may interact with a system backend (such as server 104, FIG. 1). Such an application may be developed using programming techniques as are known in the art. The application may use a touch screen, and may use icons, buttons, touch-sensitive areas, or a combination of the above, or other input means for interacting with a user; where one or more of these terms are used below, it should be understood that the others could be substituted. Heuristics may be used to allow a user to operate the application with a minimum of mental energy and time, and the application may have only a subset of its functionality available on any one screen, so that choices can rapidly be understood and selected by the user without undue mental effort.

When a worker selects icon 1201, the application may execute to present further screens through which information forming a problem report may be entered. That information may be packaged as a report and forwarded, using any communication media accessible to the device on which the application executes. In some embodiments, the application may be executed in or from a web browser, such as Mobile Safari, Google Chrome, or another browser. In some embodiments, the application may be a stand-alone executable. In some embodiments, the application may be a part of another application, such as an application for general health services delivery, or an general-purpose application for use by users of a particular company, or another application. Icon 1201 may appear as one of a plurality of other application user interface features, in some embodiments, such as when the reporting system application is part of another application.

Figure 13:
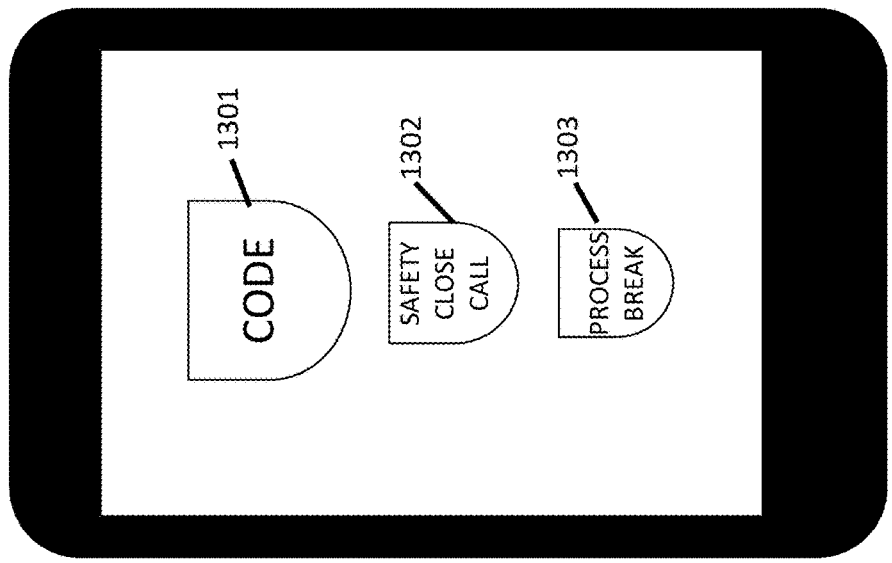

In this example, execution of the application presents screens successively that prompt the worker to input multiple types of information that collectively form the problem report. FIG. 13 illustrates a screen in which a worker is prompted to select one of multiple problem report types, each type for providing information about a problem with a given severity. In this example, three options are presented, reflecting different levels of severity, namely, CODE 1301, Safety Close Call 1302, and Process Break 1303.

In the hospital setting, "CODE" is used by some medical practitioners to indicate a patient requiring immediate resuscitation or otherwise in need of immediate medical attention, such as for a cardiac arrest. Other medical practitioners may use the term "CODE" as part of an emergency response system for identifying one of a number of emergency scenarios, such as a fire (e.g., Code Red), a bomb threat, a combative person, or an evacuation. CODE 1301 is thus provided as an option for reporting a problem that requires immediate attention. The specific type of code may be identified in a subsequent screen. Reflecting its greater urgency, CODE 1301 is made readily identifiable by one or more of a larger typeface, a larger button, a larger touch area on the touch screen, a brighter color, a position that is above other buttons on the screen, animation, or via another method. CODE 1301, when pressed, directs the user to the screen of FIG. 14.

Safety Close Call 1302 is provided below the button for CODE 1301, and its position under the CODE button reflects the lesser relative importance of a situation which has not resulted in an immediate, emergent situation but nevertheless requires urgent attention to prevent such a situation from occurring in the future. Examples of safety close calls that would be reported using button 1302 may include malfunctioning or inoperable safety equipment such as a broken wall-mounted defibrillator or fire alarm. Other examples may include conditions identified by medical practitioners. For example, if the problem reporting system described herein is adapted for use by doctors, medical close calls such as the prescription of unnecessary drugs, or the administration of the wrong drugs before surgery, such as anticoagulants before heart surgery, may be reported using this system, among other examples. Other examples may include medical issues that are identified by medical practitioners and that are not life-threatening. For example, patient falls and broken bones may be reported as "close calls." Safety Close Call 1302, when pressed, directs the user to the screen of FIG. 15.

Process Break 1303 is provided below the button for Safety Close Call 1302, and reflects the lesser relative importance of a situation which may not cause an emergency situation to occur, but nevertheless requires attention to improve the performance of hospital operations or systems. Examples of process breaks may include such issues as: a broken door or other physical fixture; stock-outs of common supplies such as latex gloves in an examination room; or a general lack of cleanliness in a particular area of the hospital. Even though such issues are relatively minor, they still require attention, and the problem reporting system described herein may enable such issues to be attended to in a timely manner. Further, each of the situations for which problem reporting is described may be the result of a complex chain of causes that may, analysis and/or aggregation, may reveal operation failings that will eventually lead to more severe problems. Once problem reports are aggregated, solutions to systemic problems that may touch on multiple separate problem reports may become identifiable, as described elsewhere herein. Specifically, with respect to process breaks, aggregation of process breaks may enable helpful modifications to processes and protocols. Process Break 1303, when pressed, directs the user to the screen of FIG. 16.

FIGS. 14-17 illustrate operational screens by which problem reports may be entered and submitted, in some embodiments.

FIG. 14 illustrates an operational screen by which a menu-driven interface allows a user to select one of a series of codes for a "CODE"-level severity problem report submission. Shown are navigational button 1401, location entry field 1402, pick list 1403, and submission button 1404. Navigational button 1401, labeled "back to list," returns the user to the screen shown in FIG. 13, thereby allowing the user to select from the list of problem reports by severity. Location entry field 1402 is shown with a value reflecting the current location of the user. In some embodiments, location entry field 1402 is automatically populated based on input from sensors on the smartphone or hardware device being operated by the user, thereby not requiring the user to spend any time identifying the current location. In some embodiments, when location information is not available from the hardware, a pick list may be provided for the location in place of a keyboard and text field, thereby saving time over free text entry. The location may be associated with the problem report when the report is submitted. Pick list 1403 includes a small number of items which can be selected, by finger as shown or by another selection device, to further identify the type of problem. In some embodiments pick list 1403 may be scrolled. Here, pick list 1403 reflects the CODE problem severity (i.e., "Code Blue," "Code Red," etc., appear in the list). Pressing or selecting submission button 1404 causes the report to be submitted.

FIG. 15 illustrates an operational screen by which a menu-driven interface allows a user to select from a predetermined list of issues in a "close call"-level severity problem report submission. Shown are navigational button 1501, location entry field 1502, pick list 1503, and submission button 1504. Navigational button 1501, labeled "back to list," returns the user to the screen shown in FIG. 13. Location entry field 1502 is shown with a value reflecting the current location of the user, which may be automatically populated as described above. The location may be associated with the problem report when the report is submitted. Pick list 1503 includes a small number of items which can be selected to further identify the type of problem. In some embodiments pick list 1503 may be scrolled. Here, pick list 1503 reflects the "close call" problem severity (i.e., "Patient Fall," "Mis-Med" (mis-medication), "infection risk" appear in the list). In some embodiments, abbreviations may be used to make the menu items more concise and to increase recognition speed in specialized work environments such as a hospital. Pressing or selecting submission button 1504 causes the report to be submitted.

Figures 16, 17:
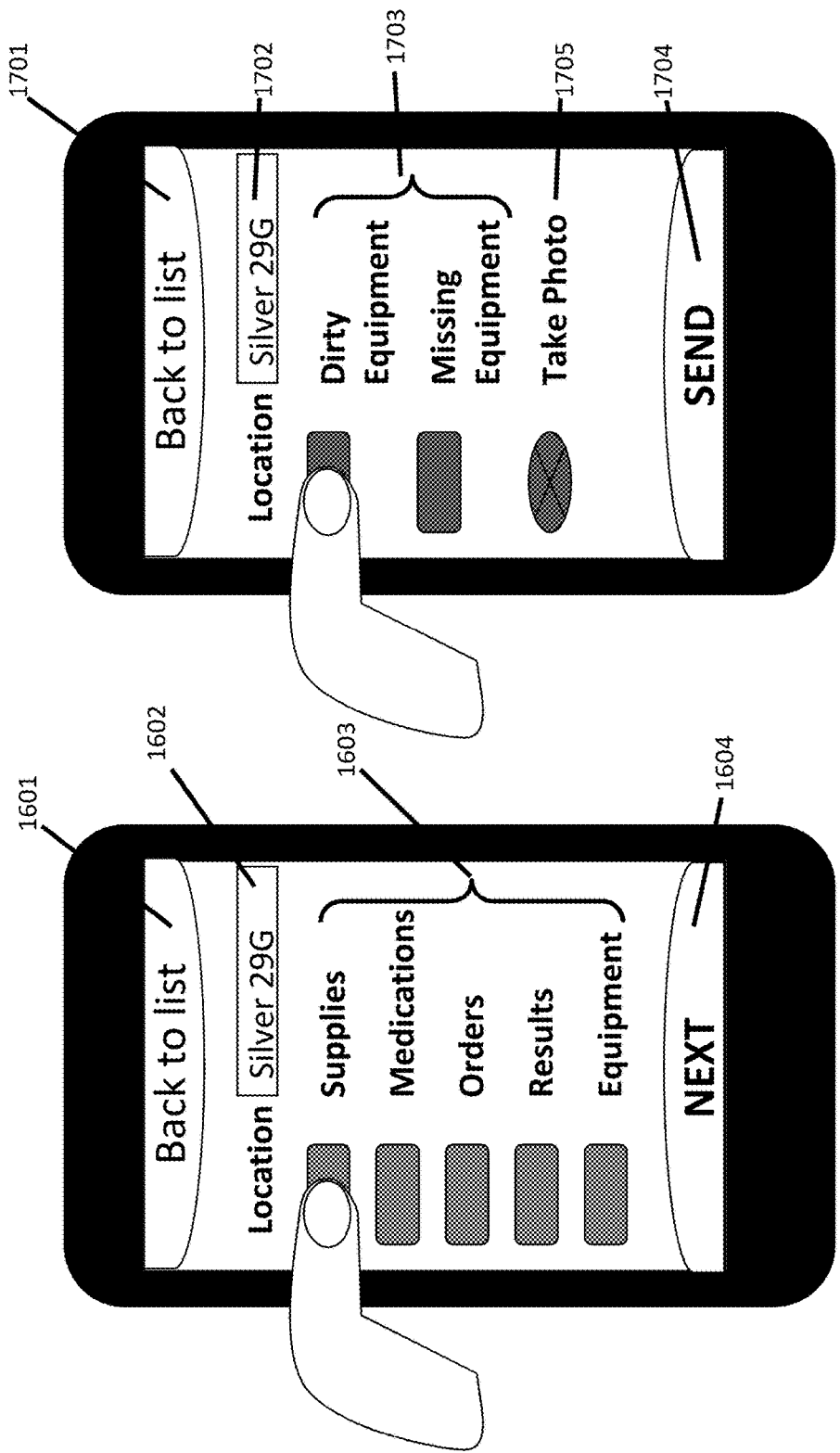

FIG. 16 illustrates a first operational screen by which a "process breakdown"-level severity problem report may be submitted. Shown are navigational button 1601, location entry field 1602, pick list 1603, and navigational button 1604. Navigational button 1601, labeled "back to list," returns the user to the screen shown in FIG. 13. Location entry field 1602 is shown with a value reflecting the current location of the user, which may be automatically populated as described above. The location may be associated with the problem report when the report is submitted. Pick list 1603 includes a small number of items which can be selected to further identify the type of problem. In some embodiments, multiple screens of pick lists may be used to allow the user to select one of a large number of items in a hierarchical organization without forcing the user to scroll through a lengthy non-organized list of items. Here, pick list 1603 reflects the "process break" problem severity. Many problems may constitute a "process break," and some types of "process break" are shown, e.g., process breaks caused by shortages in one of the list of: supplies, medications, orders, results, and equipment. Pressing or selecting button 1604 causes the next level of the pick list to be shown, as illustrated in FIG. 17.

FIG. 17 illustrates a second operational screen by which a "process breakdown"-level severity problem report may be submitted. FIG. 17 may be reached from the screen of FIG. 16. Shown are navigational button 1701, location entry field 1702, pick list 1703, and submission button 1704. Navigational button 1701 returns the user to the screen shown in FIG. 13. Location entry field 1702 behaves like location entry field 1602. Pick list 1703 includes a list of second-level items in the hierarchically-organized taxonomy shared with pick list 1603, i.e., dirty equipment, missing equipment. The application also permits the user to take a photo by selecting button 1705. A hierarchically-organized taxonomy may be used for any embodiment described herein. Pressing or selecting submission button 1704 causes the report to be submitted.

Figures 18, 19:
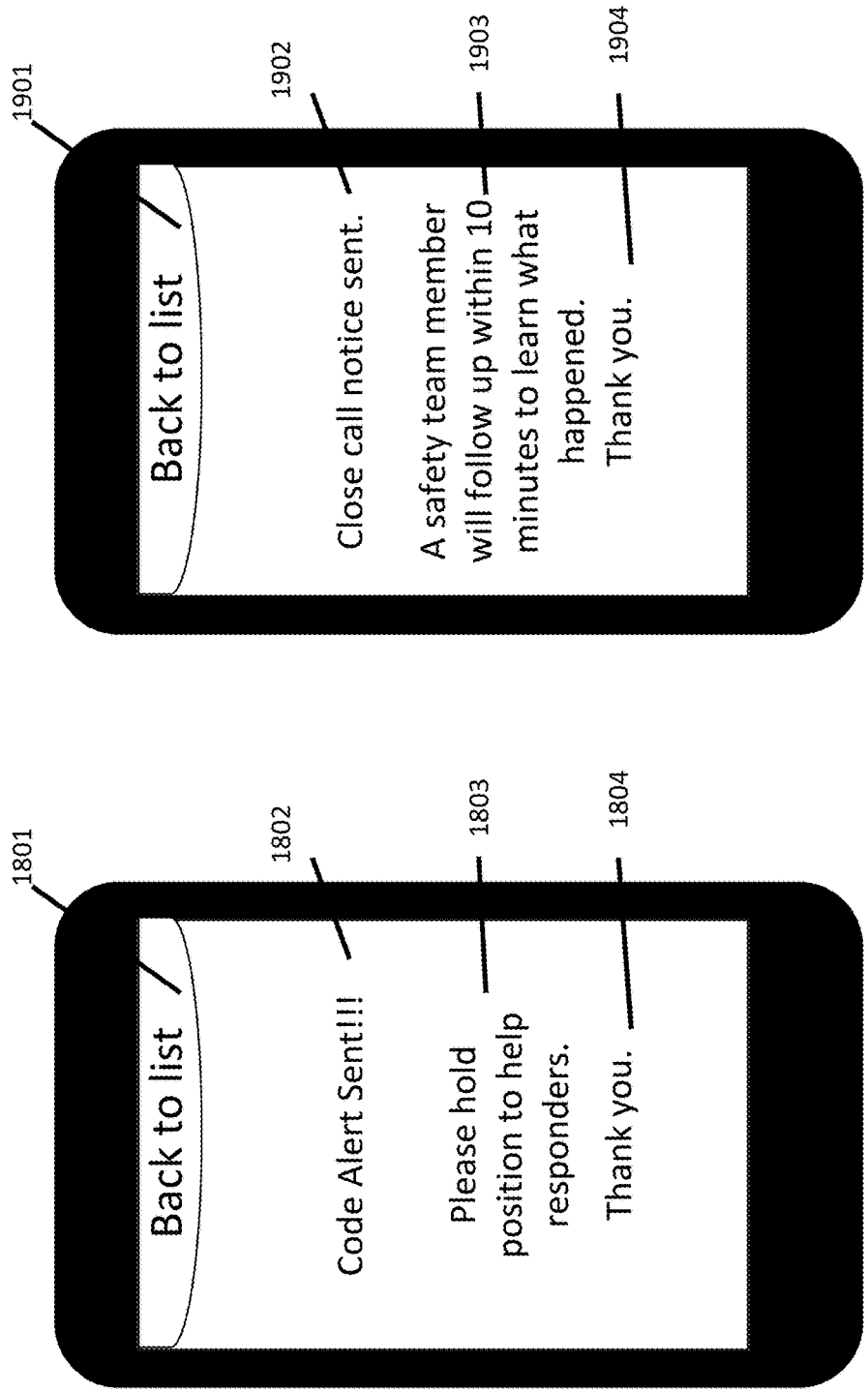
Figure 20:
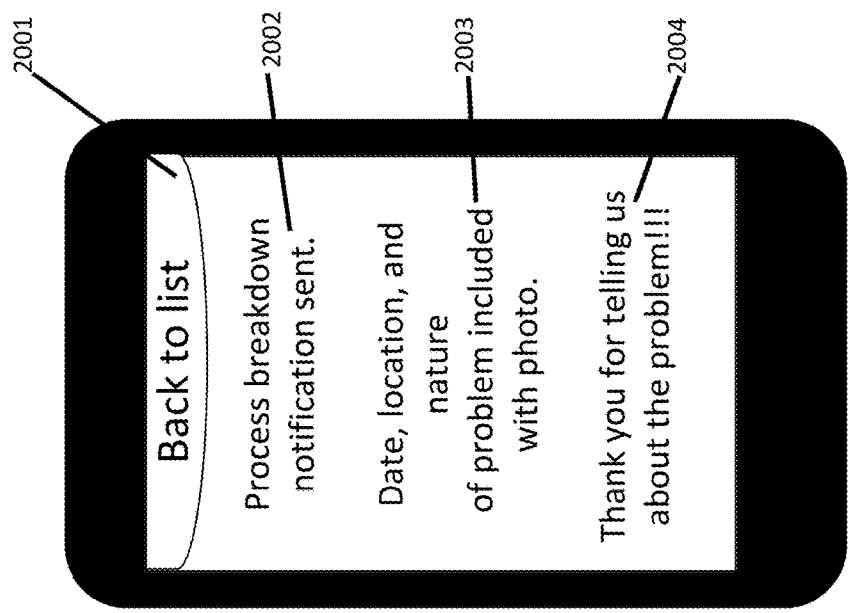

FIGS. 18-20 illustrate confirmation screens in which submission of the problem report has been completed, and this status is being reported to the worker-user, in some embodiments. However, it should be appreciated that, instead of or in addition to providing status, some or all of the depicted screens may provide feedback or instructions to the worker reporting a problem. In some embodiments each of the status screens include specific components, which are described further below.

FIG. 18 illustrates a confirmation screen for a "CODE"-level severity problem report submission. In FIG. 18, a confirmation message 1802 is displayed, indicating that the problem report has been submitted. In some embodiments, the level of severity is reflected by the message as well. The display of a confirmation message allows the user to immediately exit the problem reporting application and return to the activity he or she was previously engaged in. Also displayed are instructional message 1803, giving the user appropriate instructions for how to respond to the problem, and thank you message 1804, thanking the user for submitting the problem report. Here, since the problem being reported is urgent, the instructional message instructs the user to stay in place to assist first responders.

Also displayed is button 1801 for returning to a different screen of the program, such as a list screen, a home screen, a default screen, a start screen, or another screen. An example of such a screen is the screen of FIG. 13, and button 1804 is labeled "Back to List." Button 1804 may return the user to the list of problem report types shown in FIG. 13. However, a different message or an icon could be used for button 1804, or a different target screen may be used. Actuation of button 1804 is not required, and typically the user may return to the higher-priority activity he or she was engaged in previously.

FIG. 19 illustrates a confirmation screen for a "close call"-level severity problem report submission. Confirmation message 1901, instructional message 1902, thank you message 1904, and button 1901 are displayed. Each of the messages is modified to reflect that the problem report is for a "close call"-level severity problem. Here, since the problem being reported is not as urgent as a "CODE" alert, the instructional message indicates that the user does not need to stay in place, but rather that a team member will follow up on the report.

FIG. 20 illustrates a confirmation screen for a "process breakdown"-level severity problem report submission. Confirmation message 2001, instructional message 2002, thank you message 2003, and button 2004 are displayed. Each of the messages is modified to reflect that the problem report is for a "process breakdown"-level severity problem. Here, since the problem being reported is less urgent than a "close call" or "CODE," the message is purely informational. In some embodiments, informational message 2002 may contain specific and detailed information about the problem report that was submitted, as with notification message 1101 shown in FIG. 11.

Once information from problem reports is received, it may be aggregated and analyzed. The aggregated and analyzed information may be used in any of multiple ways. In some embodiments or scenarios, aggregated information may be used to send alerts to maintenance workers or other first responders who can address current problems. Alternatively or additionally, the report may be sent to process managers, who can make process changes to address both current and future problems. Moreover, the information may be made available to one or more users of the problem reporting system as a more general management tool. Information, for example, may inform about performance of the organization or other metrics useful in making management decisions. This information may be presented in the form of a static report. In some embodiments, the information may be available through a website, allowing a user to provide criteria that selects information for presentation and the manner in which that information is presented.

Figure 21:
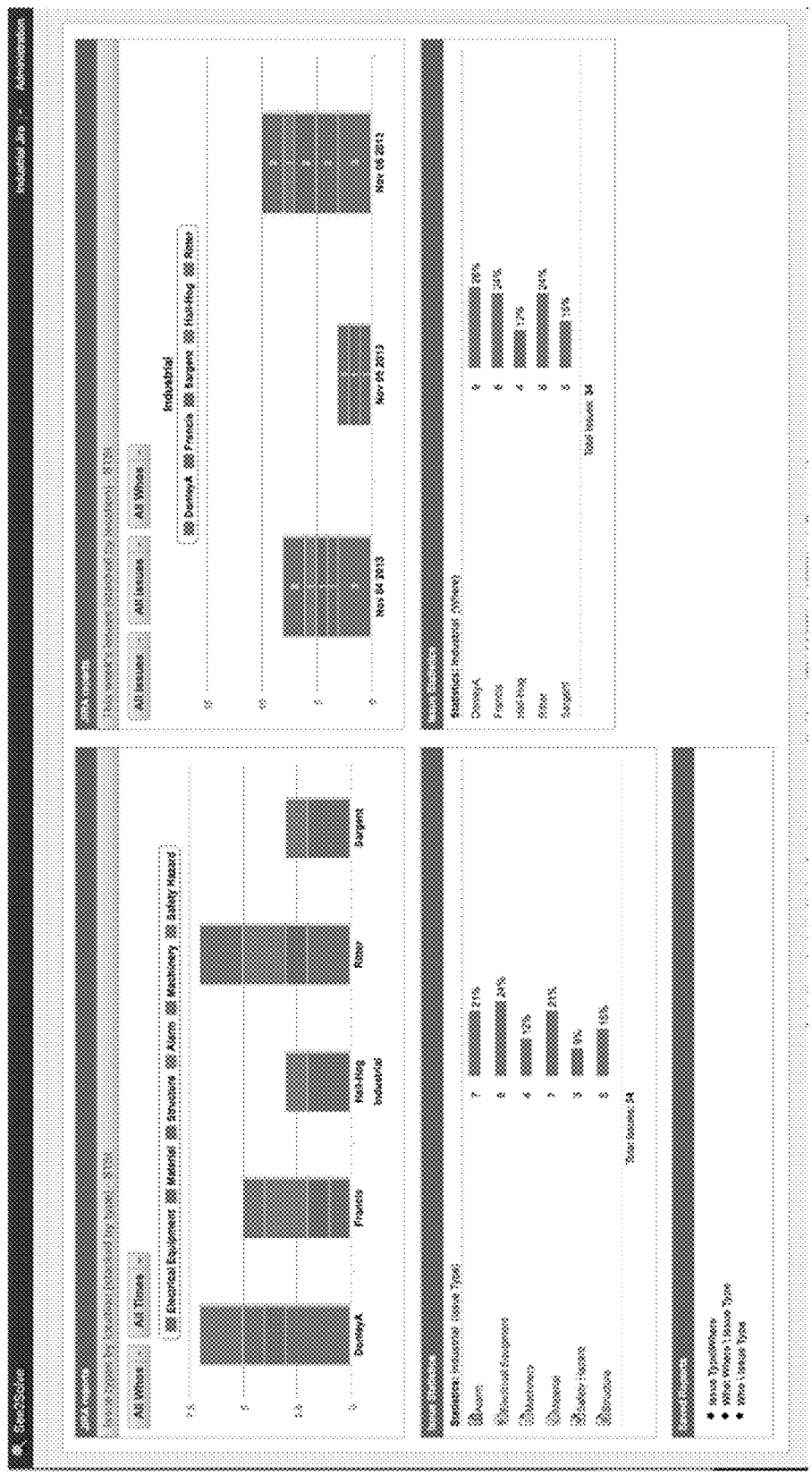
FIG. 21 illustrates an analytics interface, in accordance with some embodiments.

FIG. 21, for example, shows a graphical user interface through which a user may access aggregated information. The user interface may be rendered by a computing device (such as server 104) that receives user input identifying characteristics of information to be displayed. The computing device may dynamically present controls on the user interface that allow a user to specify types of problem reports about which information is desired. Alternatively or additionally, using such controls, the user may specify one or more other criterion, such as location, worker reporting a problem, time span, severity or any other criteria.

FIG. 21 illustrates a graphical user interface with multiple display areas, each showing a different type of information. Such a display may serve as a dashboard for problems within an organization. Managers may access such a dashboard to determine how to efficiently schedule maintenance, dispatch first responders or otherwise address existing or potential problems within an organization. FIG. 21 shows information that may be accessed by one manager. Other managers may access other collections of information. In a problem reporting system as described herein, the computerized devices forming the backend of the system may present a user interface is customized for each manager, and different such user interfaces may be presented to different users at different times.

The selected information may be presented in any suitable way. In some embodiments, the information may be presented graphically. For example, FIG. 21 illustrates a bar chart showing problem reports by location. Color coding may be used to indicate the frequency of occurrence of each of multiple types of problem. Such reporting may be facilitated in a system that supports a finite number of problem types. A bar chart showing relative numbers of problem reports and each of multiple locations may presents a "heat map" to that user. A heat map can highlight locations where there is a significant frequency of occurrence of problems ('hot spots'), as well as locations with few problems ('quiet zones') and areas where there is a problematic absence of data ('blind spots').

Aggregation may also include analytics for analysis of numerical parameters, when such parameters are reported (e.g., the number of bandages remaining in a box), concentrations of problems within designated zones, categorizations of problem types, identification of changing trends of categories or numerical values over time, or other parameters.

Multiple small issue reports may be aggregated to infer or identify problems early. This is possible because the significant decrease in problem reporting time increases the number and frequency of problem reports and thus enables the analysis of current, relevant process data. Leading indicators of system vulnerability may thus be identified, and immediate response may be enabled.

It should be appreciated that a bar chart is just one example of a graphical technique for depicting problem frequency by location. Similar information may be conveyed, for example, by literally presenting a map with different locations shown in graphically distinct ways to signify frequency of occurrence of problems. For example, different colors may be used to identify locations with a higher and lower number of problems or with problems of higher or lower severity.

Figure 22:
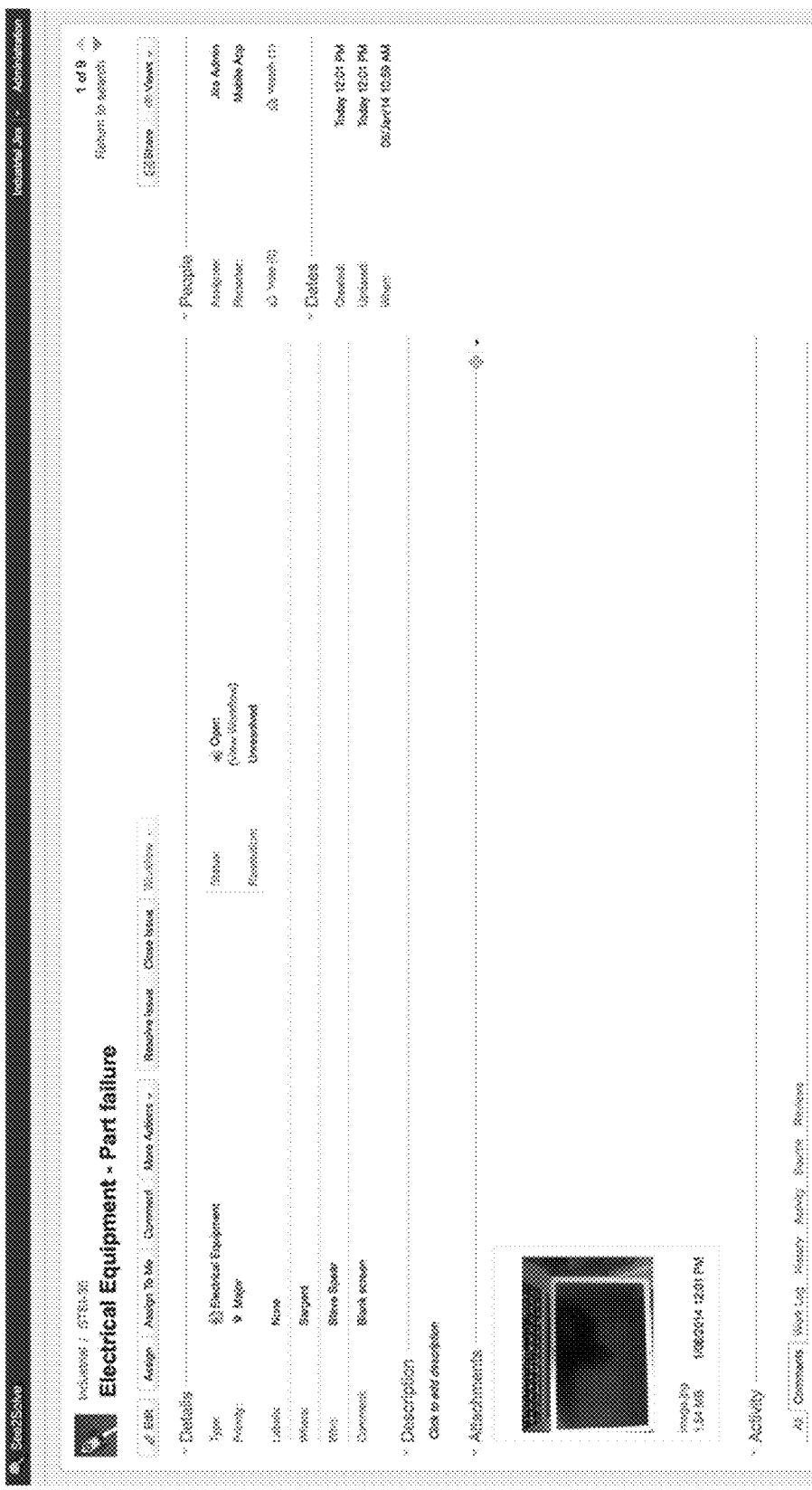
FIG. 22 illustrates an alternative analytics interface, in accordance with some embodiments.

A dynamic graphical user interface is illustrated in FIG. 21 may enable a user to drill down and obtain additional information about problems. FIG. 22 illustrates an alternative graphical user interface through which a manager or other user may access information generated by processing problem reports. In this example, information about an identified problem is presented to such a user. The information presented through a graphical user interface as illustrated in FIG. 22 may represent a single problem report or a single problem identified by aggregating multiple problem reports. Information such as location, time or the nature of the reported problem may be accessed through such user interface. Similarly, annotations submitted with the problem report may be accessed. Such information may be used to identify or respond to a reported problem. Issue reports may be integrated with workflow and task management.

Having thus described several aspects of at least one embodiment of this invention, it is to be appreciated that various alterations, modifications, and improvements will readily occur to those skilled in the art.

For example, embodiments were described in which communication is predominantly one-way, with information flowing from an incident site to the system backend. Such a flow of information supports problem identification and scheduling maintenance or other corrective action. However, in some embodiments, a communication channel alternatively or additionally may support communication from the system backend to the incident site. Such communication may enable instructions or other information for responding to a situation to be provided to someone at the incident site. Such information, for example, may be provided to a worker reporting a problem and may include instructions for securing the site or taking other immediate action. Such information may also be provided to a responder dispatched to the site. For example, information flow in this direction may provide a wiring diagram to a service technician for an unfamiliar piece of equipment requiring repair or may otherwise provide information that aides in the dressing a problem. This information may be provided automatically or may be provided by a human user interacting with the system backend.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semicustom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A communication system for processing problem reports within an organization, wherein problems may be encountered by workers and may be addressed by one or more support personnel, the system comprising:
   a communication interface, wherein the communication interface is configured to receive reports from portable computing devices used by the workers, and the reports are based on selections made through a menu-based interface through which a user may specify at least a problem type and a severity, wherein at least some of the selections are made by the user providing one-handed user input to the menu-based interface of one of the portable computing devices;
   a non-transitory computer readable storage media storing a mapping from a problem type and a severity to support personnel in one of a plurality of support levels within the organization, wherein the mapping includes information specifying a first support level associated with a higher severity and a second support level associated with a lower severity; and
   a server configured to:
      process reports received through the communication interface, wherein the processing comprises, for each report of at least a portion of the reports:
         identifying one of the plurality of support levels based on applying the problem type and the severity contained in the report to the mapping; and
         selecting, based on applying the selections contained in the report to the mapping, at least one support person belonging within the identified support level as a recipient of information contained in the report; and
      transmitting information derived from the report to a computing device associated with the selected support person.

2. The system of claim 1, wherein the system further comprises a user interface, wherein the mapping is received through the communication interface.

3. The system of claim 1, wherein:
   processing the reports comprises aggregating a plurality of reports so as to identify a problem and a severity based on the plurality of reports;
   identifying at least one second-level support person based on the identified problem and severity; and
   transmitting information derived from the aggregated reports to a computing device associated with the identified second-level support person.

4. The system of claim 3, wherein aggregating the plurality of reports comprises identifying a subset of reports from the plurality of reports based on contextual information such that each report among the subset of reports relates to similar contextual information.

5. The system of claim 3, wherein processing the reports further comprises identifying a type of response based on the severity and the identified problem.

6. The system of claim 3, wherein aggregating the plurality of reports comprises identifying a subset of reports from the plurality of reports having a low severity level and aggregating the subset of reports to identify a systemic problem within the organization.

7. The system of claim 6, wherein aggregating the plurality of reports comprises aggregating a plurality of reports obtained over time and monitoring the systemic problem over time.

8. The system of claim 3, processing the reports further comprises scheduling a visit of at least one support person suitable for responding to the identified problem based on the severity and the identified problem.

9. The system of claim 1, wherein the processing further comprises analyzing the report to determine the problem type and the severity indicated by the selections made by the user and identifying the at least one support person that corresponds to the problem type and the severity indicated by the mapping.

10. The system of claim 1, wherein identifying the at least one support person comprises identifying a level of support within the organization suitable for responding to the identified problem based on the severity and selecting at least one support person associated with the level of support.

11. The system of claim 1, wherein the server is further configured to transmit response information to a portable computing device having the menu-based interface.

12. The system of claim 11, wherein the response information indicates a corrective instruction for resolving the problem.

13. At least one non-transitory computer-readable storage medium storing computer-executable instructions that, when executed by a processor, perform a method of reporting a problem within an organization by analyzing user input provided by a worker encountering the problem through a user interface of at least one computing device, wherein the user interface is configured to present a plurality of choices indicating possible conditions to report, the method comprising:

acquiring contextual information identifying the worker and a location of the worker;

identifying a first set of choices from among the plurality of choices to present on the user interface based on the contextual information;

identifying, dynamically, a second set of choices from among the plurality of choices to present on the user interface based on user input indicating selection of a first choice from among the first set of choices, wherein the second set of choices includes conditions within a category constrained by the condition identified by the first choice; and generating a report constructed from information provided by the first choice and a second choice selected from among the second set of choices by user input indicating selection of the second choice, wherein a combination of the first choice and the second choice specifies a problem associated with the location of the worker and the report identifies the problem.

14. The at least one non-transitory computer-readable storage medium of claim 13, wherein identifying the second set of choices comprises identifying possible second level conditions categorized by the first choice.

15. The at least one non-transitory computer-readable storage medium of claim 13, wherein the method further comprises receiving an indication confirming transmission of the report over a network to at least one second computing device associated with at least one support person.

16. The at least one non-transitory computer-readable storage medium of claim 15, wherein the method further comprises receiving response information indicating a corrective instruction provided by the at least one second computing device based on input by the at least one support person.

17. The at least one non-transitory computer-readable storage medium of claim 13, wherein identifying the first set of choices from among the plurality of choices comprises analyzing contextual information related to a type of work the worker performs.

18. A method of reporting a problem encountered by a worker to at least one support person of an organization by analyzing a user input provided by the worker to a user interface associated with at least one computing device, the method comprising:

identifying, based on a type of work performed by the worker, a plurality of choices that indicate possible conditions of different types of problems associated with the type of work, wherein the plurality of choices is organized in hierarchical layers based on contextual information associated with the organization;

presenting, by the user interface, the plurality of choices by dynamically presenting choices corresponding to one hierarchical layer at a time;

receiving, from the worker, user input indicating selection of a portion of choices from the plurality of choices such that the selected portion of choices are from different hierarchical layers;

constructing a report indicating conditions based on the selected portion of choices;

identifying, based on the selected portion of choices, a support level from among a plurality of support levels in the organization; and selecting, based on the selected portion of choices and information indicating availability of managers within the identified support level, at least one manager in the identified support level as a recipient for the report.

19. The method of claim 18, wherein the plurality of choices is organized based on contextual information identifying a role of the worker within the organization.

20. The method of claim 18, wherein the selected portion of choices indicates a type of problem encountered by the worker.

21. The method of claim 18, the method further comprising receiving response information indicating a corrective instruction provided by the at least one second computing device based on input by the at least one manager.

22. The method of claim 18, wherein a combination and an order of the selected portion of choices identifies the support level.

23. A portable electronic device comprising:

a display configured to display a menu-based interface; and control circuitry configured to perform a method comprising:

identifying a first set of choices from among a plurality of choices based on contextual information identifying a worker associated with the portable electronic device, wherein the plurality of choices indicates conditions of problems and is organized in hierarchical layers, and the first set of choices is associated with a first layer of the hierarchical layers;

presenting the first set of choices as menu options on the menu-based interface;

receiving, from the worker, user input indicating selection of a first choice from among the first set of choices;

identifying, dynamically, a second set of choices from among the plurality of choices based on the selected first choice, wherein the second set of choices is associated with a second layer of the hierarchical layers constrained by the selected first choice; and generating a report constructed from information provided by the selected first choice and a second choice selected from among the second set of choices by user input indicating selection of the second choice, wherein a combination of the selected first choice and the selected second choice specify a type of problem encountered by the worker.

24. The portable electronic device of claim 23, wherein the second set of choices indicates possible conditions within a category identified by the selected first choice.

25. The portable electronic device of claim 23, wherein the control circuitry is further configured to present the second set of choices as menu options on the menu-based interface in response to the user input indicating the selected first choice.

26. The portable electronic device of claim 25, wherein the control circuitry is further configured to transmit the report and present response information on the display indicating transmission of the report.

27. The portable electronic device of claim 23, wherein the device further comprises at least one sensor configured to provide the contextual information including a location of the portable electronic device.

28. The portable electronic device of claim 23, wherein the device further comprises at least one computer readable storage media storing identification information of the worker and identifying a first set of choices from among a plurality of choices comprises identifying the first set of choices based on the identification information.

29. The at least one non-transitory computer-readable storage medium of claim 13, wherein acquiring contextual information further comprises obtaining the location of the worker from at least one sensor of the at least one computing device.

* * * * *